US011330821B2

(12) United States Patent
Shanahan et al.

(10) Patent No.: US 11,330,821 B2
(45) Date of Patent: May 17, 2022

(54) HERBICIDAL COMPOUNDS

(71) Applicant: Syngenta Participations AG, Basel (CH)

(72) Inventors: Stephen Edward Shanahan, Bracknell (GB); Timothy Jeremiah Cornelius O'Riordan, Bracknell (GB)

(73) Assignee: Syngenta Participations AG, Basel (CH)

( * ) Notice: Subject to any disclaimer, the term of this patent is extended or adjusted under 35 U.S.C. 154(b) by 855 days.

(21) Appl. No.: 15/570,045

(22) PCT Filed: Apr. 27, 2016

(86) PCT No.: PCT/EP2016/059378
§ 371 (c)(1),
(2) Date: Oct. 27, 2017

(87) PCT Pub. No.: WO2016/174072
PCT Pub. Date: Nov. 3, 2016

(65) Prior Publication Data
US 2018/0116219 A1 May 3, 2018

(30) Foreign Application Priority Data

Apr. 30, 2015 (GB) .................................... 1507464

(51) Int. Cl.
| | | |
|---|---|---|
| *A01N 43/58* | (2006.01) | |
| *C07D 401/12* | (2006.01) | |
| *C07C 53/18* | (2006.01) | |
| *C07D 417/12* | (2006.01) | |
| *A01N 43/78* | (2006.01) | |
| *C07D 409/12* | (2006.01) | |
| *C07D 403/12* | (2006.01) | |
| *A01N 43/60* | (2006.01) | |
| *C07D 413/12* | (2006.01) | |
| *A01N 43/76* | (2006.01) | |
| *C07D 239/54* | (2006.01) | |

(52) U.S. Cl.
CPC ............. *A01N 43/58* (2013.01); *A01N 43/60* (2013.01); *A01N 43/76* (2013.01); *A01N 43/78* (2013.01); *C07C 53/18* (2013.01); *C07D 239/54* (2013.01); *C07D 401/12* (2013.01); *C07D 403/12* (2013.01); *C07D 409/12* (2013.01); *C07D 413/12* (2013.01); *C07D 417/12* (2013.01)

(58) Field of Classification Search
CPC ........ A01N 43/58; A01N 43/60; A01N 43/76; A01N 43/78; C07C 53/18; C07D 239/54; C07D 401/12; C07D 403/12; C07D 409/12; C07D 413/12; C07D 417/12

USPC ........................................................ 504/238
See application file for complete search history.

(56) References Cited

U.S. PATENT DOCUMENTS

| | | | | |
|---|---|---|---|---|
| 9,604,983 | B2 * | 3/2017 | Shanahan ............ | C07D 471/04 |
| 9,944,608 | B2 * | 4/2018 | Shanahan ............ | C07D 237/16 |
| 10,292,394 | B2 * | 5/2019 | Shanahan ............ | C07D 471/04 |
| 10,385,063 | B2 * | 8/2019 | Shanahan ............ | C07D 241/42 |
| 2009/0111696 | A1 * | 4/2009 | Kiji ....................... | C07C 251/76 |
| | | | | 504/238 |
| 2010/0173775 | A1 * | 7/2010 | Lehr .................... | C07D 237/16 |
| | | | | 504/103 |
| 2010/0216642 | A1 * | 8/2010 | Fusaka ................. | C07D 237/16 |
| | | | | 504/238 |
| 2011/0118118 | A1 * | 5/2011 | Lehr .................... | C07D 237/16 |
| | | | | 504/103 |
| 2012/0028803 | A1 * | 2/2012 | Fusaka .................. | A01N 43/58 |
| | | | | 504/238 |
| 2012/0028988 | A1 * | 2/2012 | Sakamoto .............. | A01N 43/58 |
| | | | | 514/252.03 |
| 2013/0281299 | A1 * | 10/2013 | Kuragano .............. | A01N 43/58 |
| | | | | 504/237 |

FOREIGN PATENT DOCUMENTS

| | | |
|---|---|---|
| JP | 2012/056903 A | 3/2012 |
| JP | 2014/210806 A | 11/2014 |
| WO | 2007/119434 A1 | 10/2007 |
| WO | 2009/086041 A1 | 7/2009 |
| WO | 2011/045271 A1 | 4/2011 |
| WO | 2011/117195 A1 | 9/2011 |
| WO | 2014/119770 A1 | 8/2014 |
| WO | 2015/071205 A1 | 5/2015 |
| WO | 2015/177109 A1 | 11/2015 |

OTHER PUBLICATIONS

International Search Report for International Patent Application No. PCT/EP2016/059378 dated Jun. 1, 2016.
GB Search Report for GB Patent Application No. GB1507464.4 dated Jan. 25, 2016.

\* cited by examiner

*Primary Examiner* — Sue X Liu
*Assistant Examiner* — Mei Ping Chui
(74) *Attorney, Agent, or Firm* — BakerHostetler; Toni-Junell Herbert

(57) ABSTRACT

The present invention relates to herbicidal heteroaryl-alkyl-oxy-substituted heteroaryl/phenyl-pyridazine-diones and heteroaryl-alkyl-oxy-substituted heteroaryl/phenyl-pyridazinone derivatives of formula (I), as well as to processes and intermediates used for the preparation of such derivatives. The invention further extends to herbicidal compositions comprising such derivatives, as well as to the use of such compounds and compositions in controlling undesirable plant growth; in particular the use in controlling weeds, such as broad-leaved dicotyledonous weeds, in crops of useful plants.

15 Claims, No Drawings

HERBICIDAL COMPOUNDS

RELATED APPLICATION INFORMATION

This application is a 371 of International Application No. PCT/EP2016/059378, filed Apr. 27, 2016, which claims priority to GB Application No. 1507464.4, filed Apr. 30, 2015, the contents of which are incorporated herein by reference herein.

The present invention relates to herbicidal heteroaryl-alkyl-oxy-substituted heteroaryl/phenyl-pyridazine-diones and heteroaryl-alkyl-oxy-substituted heteroaryl-/phenyl-pyridazinone derivatives of formula (I), as well as to processes and intermediates used for the preparation of such derivatives. The invention further extends to herbicidal compositions comprising such derivatives, as well as to the use of such compounds and compositions in controlling undesirable plant growth; in particular the use in controlling weeds, such as broad-leaved dicotyledonous weeds, in crops of useful plants.

Herbicidal pyridazinones are known from WO2009/086041. In addition, herbicidal 5/6 membered heterocyclyl-substituted pyridazinones are known from WO 2011/045271. Whilst WO2013/160126 describes indolyl-pyridazinone derivatives, which exhibit herbicidal activity.

The present invention is based on the finding that heteroaryl-alkyl-oxy-substituted heteroaryl/phenyl-pyridazine-diones and heteroaryl-alkyl-oxy-substituted heteroaryl-/phenyl-pyridazinone derivatives of formula (I) exhibit surprisingly good herbicidal activity.

Thus, in a first aspect there is provided a compound of formula (I)

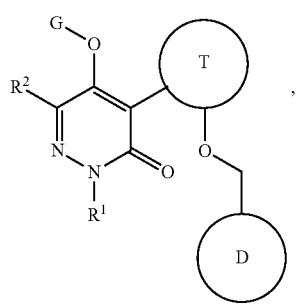

or a salt or N-oxide thereof, $R^1$ is selected from the group consisting of $C_1$-$C_4$ alkyl, $C_3$-$C_6$ cycloalkyl, $C_1$-$C_2$alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl and $C_2$-$C_4$ haloalkynyl;

$R^2$ is selected from the group consisting of hydrogen, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, $C_1$-$C_6$alkyl-S(O)$_m$—, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl; G is hydrogen, or C(O)$R^3$;

$R^3$ is selected from the group consisting of $C_1$-$C_6$alkyl, $C_1$-$C_6$alkenyl, $C_1$-$C_6$alkynyl, $C_1$-$C_6$alkoxy, $C_1$-$C_6$alkyl-S—, —NR$^4$R$^5$ and phenyl optionally substituted by one or more $R^6$; $R^4$ and $R^5$ are independently selected from the group consisting of $C_1$-$C_6$ alkyl and $C_1$-$C_6$ alkoxy, or $R^4$ and $R^5$ together can form a morpholinyl ring;

$R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy; and T is a 5- or 6-membered monocyclic heteroaryl ring system containing 1, 2, or 3 heteroatoms independently selected from nitrogen, oxygen and sulphur, said 5-membered ring system being substituted by one or more radicals selected from X, Y, and $R^7$, and said 6-membered ring system being substituted by one or more radicals selected from $X^1$, $X^2$, $X^3$, $X^4$ and $R^7$, and wherein the oxy-alkyl-D moiety and the pyridazine dione/pyridazinone moiety are linked via ring T such that they are situated ortho with respect to each other; or T is a substituted phenyl ring of formula (Tp)

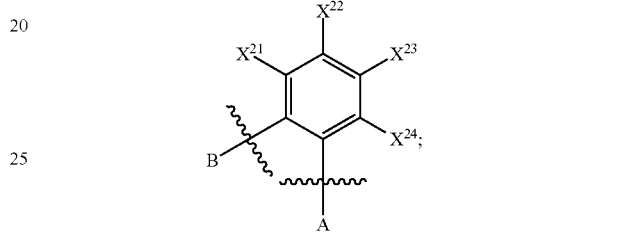

each X, $X^3$, $X^{23}$ and each Y are independently hydrogen, $C_1$-$C_3$ alkyl, $C_1$-$C_3$ alkoxy, $C_1$-$C_3$haloalkyl, $C_1$-$C_3$haloalkoxy, or halogen;

$X^1$ is oxo, $C_1$-$C_3$ alkyl, $C_1$-$C_3$ alkoxy, $C_1$-$C_3$haloalkyl, $C_1$-$C_3$haloalkoxy, or halogen;

$X^2$, and $X^4$ are independently hydrogen, $C_1$-$C_3$ alkyl, $C_1$-$C_3$ alkoxy, $C_1$-$C_3$haloalkyl, $C_1$-$C_3$haloalkoxy, oxo, or halogen;

$X^{21}$ is $C_1$-$C_3$ alkyl, $C_1$-$C_3$ alkoxy, $C_1$-$C_3$haloalkyl, $C_1$-$C_3$haloalkoxy, or halogen;

$X^{22}$, and $X^{24}$ are independently hydrogen, $C_1$-$C_3$ alkyl, $C_1$-$C_3$ alkoxy, $C_1$-$C_3$haloalkyl, $C_1$-$C_3$haloalkoxy, or halogen;

$R^7$ is hydrogen, $C_1$-$C_3$ alkyl, $C_1$-$C_3$ alkoxy, $C_1$-$C_3$haloalkyl, $C_1$-$C_3$haloalkoxy;

A denotes the point of attachment to the oxy-alkyl-D moiety and B denotes the point of attachment to the pyridazine dione/pyridazinone moiety; and D is a substituted or unsubstituted 5- or 6-membered monocyclic heteroaryl ring containing 1, 2, or 3 heteroatoms independently selected from oxygen, nitrogen and sulphur, and wherein when D is substituted it is substituted on at least one ring carbon atom with $R^9$ and/or on a ring nitrogen atom with $R^9$;

each $R^9$ is independently oxygen, hydroxyl, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, $C_1$-$C_6$alkyl-S(O)$_m$—, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;

each $R^9$ is independently, $C_1$-$C_4$ alkyl, $C_3$-$C_6$alkoxy, $C_1$-$C_2$ alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl or $C_2$-$C_4$ haloalkynyl; and m is an integer of 0, 1, or 2.

Compounds of Formula (I) may contain asymmetric centres or an axis of chirality and may be present as a single enantiomer, pairs of enantiomers in any proportion or, where more than one asymmetric centre/axis of chirality is present, contain diastereoisomers in all possible ratios. Typically one of the enantiomers has enhanced biological activity compared to the other possibilities.

Similarly, where there are di-substituted alkenes, these may be present in E or Z form or as mixtures of both in any proportion.

Furthermore, compounds of formula (I) may be in equilibrium with alternative tautomeric forms. For example, a compound of formula (I-i), i.e. a compound of formula (I) wherein $R^2$ is hydrogen and G is hydrogen, can be drawn in at least three tautomeric forms:

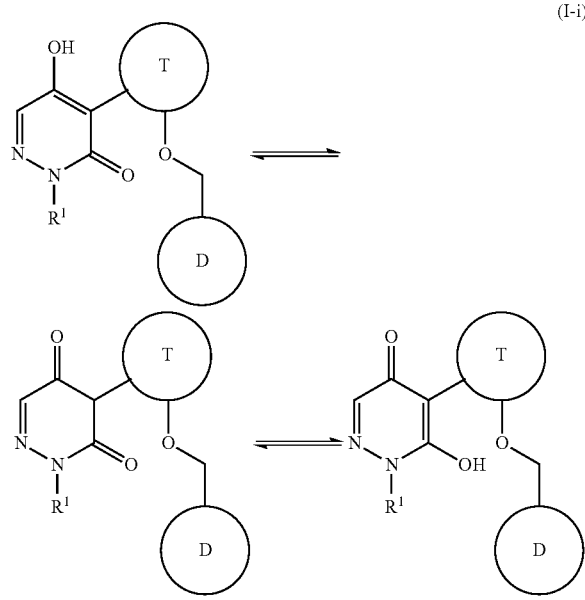

(I-i)

It should be appreciated that all tautomeric forms (single tautomer or mixtures thereof), racemic mixtures and single isomers are included within the scope of the present invention.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$alkyl groups (except where already defined more narrowly), but are preferably $C_1$-$C_4$alkyl or $C_1$-$C_3$alkyl groups, and, more preferably, are $C_1$-$C_2$alkyl groups (such as methyl).

Alkenyl and alkynyl moieties can be in the form of straight or branched chains, and the alkenyl moieties, where appropriate, can be of either the (E)- or (Z)-configuration. The alkenyl or alkynyl moieties are typically $C_2$-$C_4$alkenyl or $C_2$-$C_4$alkynyl, more specifically vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Preferably, the term cycloalkyl refers to cyclopropyl, cyclobutyl, cyclopentyl or cyclohexyl.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

The term "heteroaryl" as used herein means an aromatic ring system containing at least one ring heteroatom and consists of a single ring. Preferably, single rings will contain 1, 2 or 3 ring heteroatoms selected independently from nitrogen, oxygen and sulfur. Typically "heteroaryl" is as used in the context of this invention includes furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, and triazinyl rings, which may or may not be substituted as described herein.

The group (B)

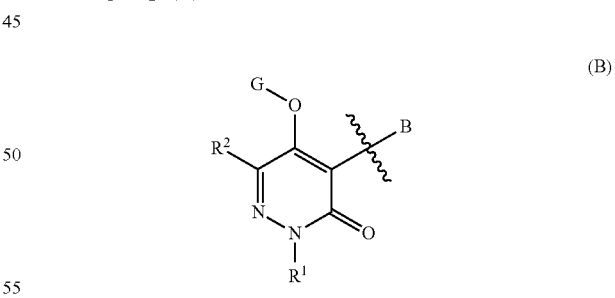

(B)

is referred to herein as the pyridazine dione/pyridazinone moiety, wherein B denotes the point of attachment to the rest of the molecule (i.e. to the optionally substituted heteroarylalkyl-oxy-heteroaryl/phenyl moiety).

The present invention also includes agronomically acceptable salts that the compounds of formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used. The compounds of formula (I) according to the invention also include hydrates which may be formed during the salt formation.

Preferred values of $R^1$, $R^2$, $R^3$, $R^4$, $R^5$, $R^6$, $R^7$, $R^8$, $R^9$, G, D, X, $X^1$, $X^2$, $X^3$, $X^4$, $X^{21}$, $X^{22}$, $X^{23}$, $X^{24}$, Y, Z, and m are as set out below, and a compound of formula (I) according to the invention may comprise any combination of said values. The skilled man will appreciate that values for any specified set of embodiments may combined with values for any other set of embodiments where such combinations are not mutually exclusive.

Preferably $R^1$ is selected from the group consisting of methyl, ethyl, propyl (in particular n- or c-propyl), or $C_1$haloalkyl. More preferably $R^1$ is methyl, ethyl, cyclopropyl, or $C_1$fluoroalkyl.

Preferably $R^2$ is selected from the group consisting of hydrogen, $C_1$-$C_6$alkyl, $C_1$-$C_6$haloalkyl, $C_1$-$C_6$alkoxy, $C_1$-$C_3$alkoxy-$C_1$-$C_3$alkyl, $C_3$-$C_6$cycloalkyl, $C_2$-$C_6$ alkenyl, $C_2$-$C_6$ haloalkenyl, $C_2$-$C_6$ alkynyl and $C_2$-$C_6$ haloalkynyl. More preferably $R^2$ is selected from the group consisting of hydrogen, methyl, ethyl, cyclopropyl, halomethyl, and methoxymethyl, more preferably still difluoromethyl, trifluoromethyl, cyclopropyl or methyl, even more preferably cyclopropyl or methyl, and most preferably methyl.

As described herein, G may be hydrogen or —C(O)—$R^3$, and $R^3$ is selected from the group consisting of $C_1$-$C_5$alkyl, $C_2$-$C_6$alkenyl, $C_2$-$C_6$alkynyl, $C_1$-$C_6$alkyl-S—, $C_1$-$C_6$alkoxy, —$NR^4R^5$ and phenyl optionally substituted by one or more $R^6$. As defined herein, $R^4$ and $R^5$ are independently selected from the group consisting of $C_1$-$C_6$ alkyl, $C_1$-$C_6$ alkoxy-; or they can together form a morpholinyl ring. Preferably $R^4$ and $R^5$ are each independently selected from the group consisting of methyl, ethyl, propyl, methoxy, ethoxy and propoxy. $R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy.

Preferably $R^3$ is $C_1$-$C_4$ alkyl, $C_1$-$C_4$alkoxy, $C_2$-$C_3$alkenyl, $C_2$-$C_3$alkynyl, $C_1$-$C_3$alkoxy, or —$NR^4R^5$ wherein $R^4$ and $R^5$ together form a morpholinyl ring. More preferably $R^3$ is isopropyl, t-butyl, methyl, ethyl, propargyl, methoxy, ethoxy or tert-butoxy.

In one set of embodiments G is hydrogen or —C(O)—$R^3$, wherein $R^3$ is $C_1$-$C_4$ alkyl, $C_2$-$C_3$alkenyl, $C_2$-$C_3$alkynyl or —$C_1$-$C_3$alkoxy. In a further set of embodiments G is hydrogen or —C(O)—$R^{3'}$ wherein $R^{3'}$ is isopropyl, t-butyl, methyl, ethyl, propargyl or methoxy. However, it is particularly preferred that G is hydrogen.

As stated above T is a 5- or 6-membered monocyclic heteroaryl ring system containing 1, 2, or 3 heteroatoms independently selected from nitrogen, oxygen and sulphur, said 5-membered ring system being substituted by one or more radicals selected from X, Y, and $R^7$, and said 6-membered ring system being substituted by one or more radicals selected from $X^1$, $X^2$, $X^3$, $X^4$ and $R^7$, and wherein the oxy-alkyl-D moiety and the pyridazine dione/pyridazinone moiety are linked via ring T such that they are situated ortho with respect to each other; or T is a substituted phenyl ring of formula (Tp)

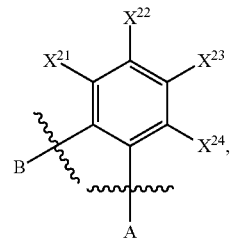

wherein $X^{21}$, $X^{22}$, $X^{23}$, $X^{24}$, A and B, are as defined herein.

Where T is a 5-membered monocyclic heteroaryl ring system, it is preferably a furyl, thienyl, pyrrolyl, pyrazolyl, imidazolyl, triazolyl, oxazolyl, isoxazolyl, thiazolyl, isothiazolyl, or oxadiazolyl ring substituted by one or more radicals independently selected from X, Y and $R^7$. Where T is a 6-membered monocyclic heteroaryl ring, it is preferably a pyridyl, pyrimidinyl, pyridazinyl, pyrazinyl, or triazinyl ring, substituted by one or more radicals independently selected from $X^1$, $X^2$, $X^3$, $X^4$ and $R^7$. In each case, it is important that the oxy-alkyl-D moiety and group B are linked via ring T such that they are situated ortho with respect to each other. With respect to the substituents (where present) $R^7$ refers to a substituent borne on a free nitrogen within the ring (by "free nitrogen" it is meant a nitrogen within ring T which is not involved in linking ring T to either group B or to the oxy-alkyl-D moiety). An $X^1$ substituent (where present) is borne on the ring atom which is ortho with respect to attachment point B, an $X^2$ substituent (where present) is borne on the ring atom which is meta with respect to attachment point B and para with respect to attachment point A, an $X^3$ substituent (where present) is borne on the ring atom which is para with respect to attachment point B, and an $X^4$ substituent (where present) is borne on the ring atom which is meta with respect to attachment point B and ortho with respect to attachment point A.

For example, T may be selected from any one of (Tp) or (T1) to (T62) as shown below, wherein A denotes the point of attachment to the oxy-alkyl-D moiety and B denotes the point of attachment to group (B):

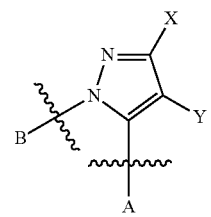

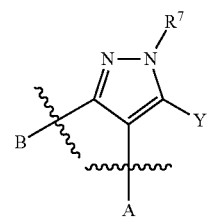

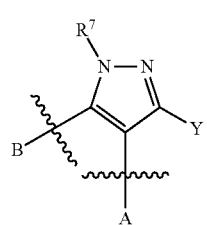 (T3)
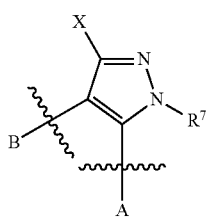 (T4)
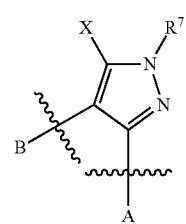 (T5)
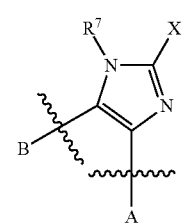 (T6)
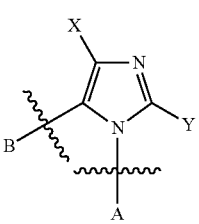 (T7)
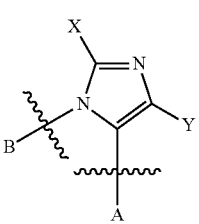 (T8)
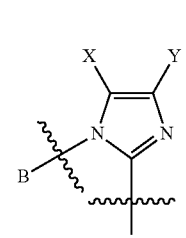 (T9)

(T17) 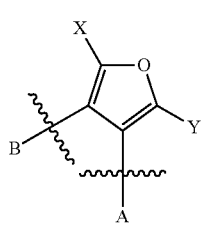
(T18) 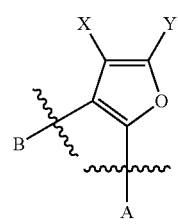
(T19) 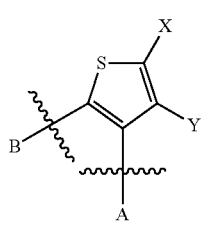
(T20) 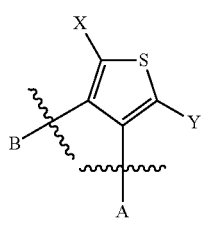
(T21) 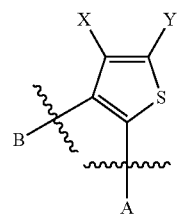
(T22) 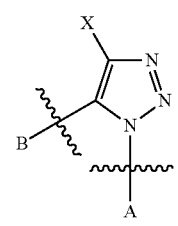
(T23) 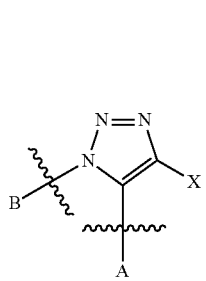
(T24) 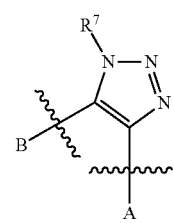
(T25) 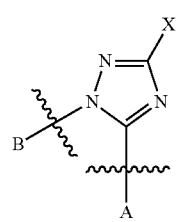
(T26) 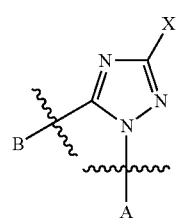
(T27) 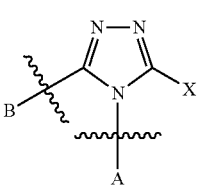
(T28) 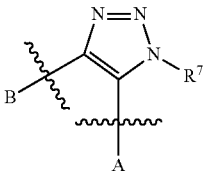
(T29) 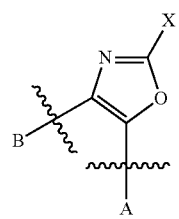
(T30) 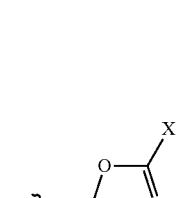

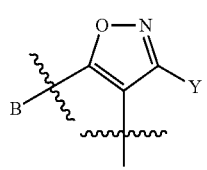 (T31)
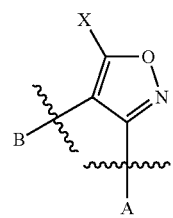 (T32)
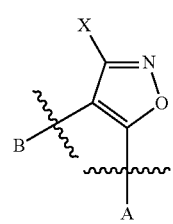 (T33)
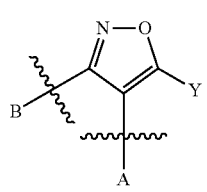 (T34)
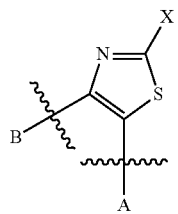 (T35)
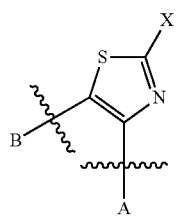 (T36)
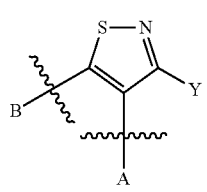 (T37)
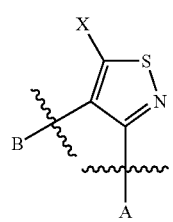 (T38)
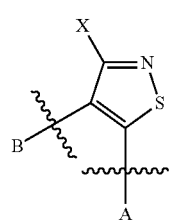 (T39)
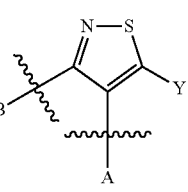 (T40)
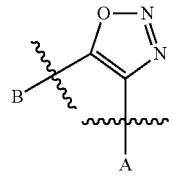 (T41)
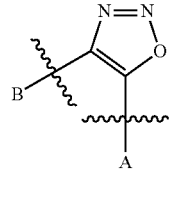 (T42)
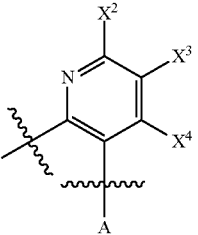 (T43)
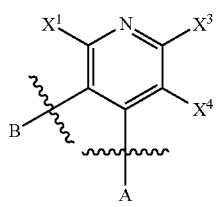 (T44)

-continued
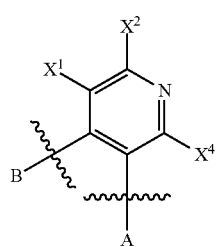 (T45)
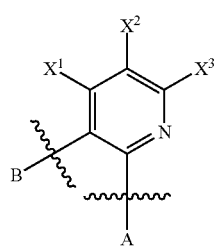 (T46)
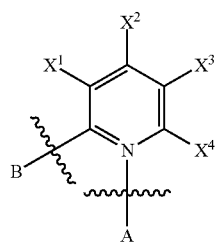 (T47)
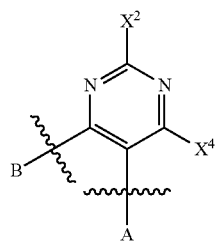 (T48)
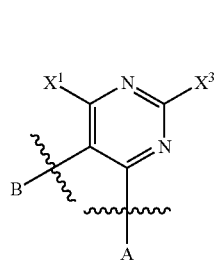 (T49)
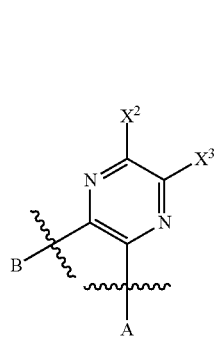 (T50)
-continued
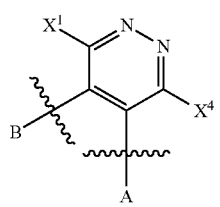 (T51)
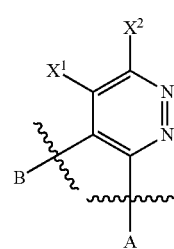 (T52)
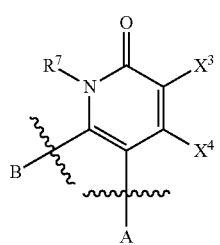 (T53)
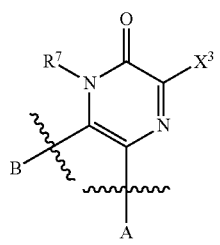 (T54)
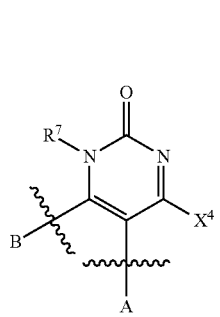 (T55)
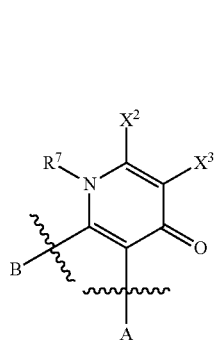 (T56)

-continued

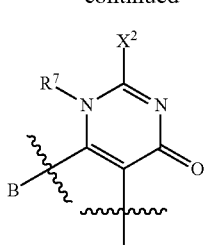 (T57)

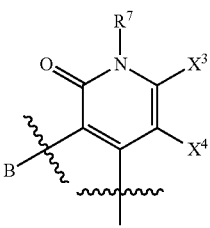 (T58)

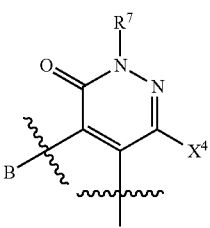 (T59)

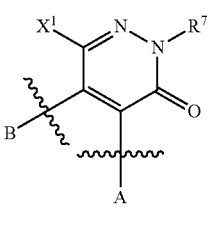 (T60)

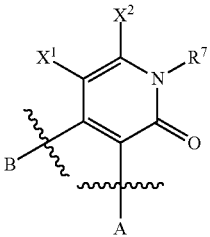 (T61)

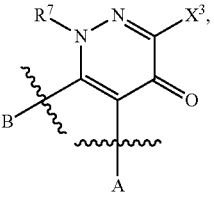 (T62)

wherein $X$, $X^1$, $X^2$, $X^3$, $X^4$, $Y$, $R^7$, are as defined herein.

From the structures above, the skilled man will appreciate that where $X^1$, $X^2$, or $X^4$ is oxo, ring T may be partially unsaturated.

In embodiments where T is (Tp), $X^{22}$ is preferably hydrogen, $X^{21}$ is preferably $C_1$-$C_3$ alkyl, $C_1$-$C_3$haloalkyl, or halogen, more preferably $C_1$-$C_3$alkyl, $C_1$haloalkyl, or halogen, even more preferably chloro, fluoro, bromo, methyl, or trifluoromethyl, and most preferably chloro, fluoro or trifluoromethyl. $X^{23}$ and $X^{24}$ are preferably independently hydrogen, $C_1$-$C_3$ alkyl, $C_1$-$C_3$haloalkyl, or halogen. More preferably $X^{23}$ and $X^{24}$ are independently chloro, fluoro, bromo, methyl, or trifluoromethyl. More preferably still, $X^{24}$ is halogen, in particular chloro.

In embodiments where T is a 5-membered monocyclic heteroaryl ring, and T bears more than one X radical, each is independently selected from hydrogen, $C_1$-$C_3$ alkyl, $C_1$-$C_3$ alkoxy, $C_1$-$C_3$haloalkyl, $C_1$-$C_3$haloalkoxy, or halogen. Where T bears an X substituent located ortho with respect to group B, that X substituent is preferably $C_1$-$C_3$ alkyl, $C_1$-$C_3$ alkoxy, $C_1$-$C_3$haloalkyl, $C_1$-$C_3$haloalkoxy, or halogen.

More preferably where T contains an X substituent that is ortho with respect to group B [e.g. in (T4), (T5), (T7), (T8), (T9), (T11), (T13), (T14), (T15), (T17), (T18), (T20), (T21), (T22), (T32), (T33), (T37), and (T38)] it is independently halogen, more preferably fluoro, chloro, or bromo, and more preferably still, fluoro or chloro.

Where T contains an X substituent located meta to either group B or to the optionally substituted oxy-alkyl-D moiety [e.g. in (T1), (T6), (T10), (T11), (T12), (T15), (T16), (T19), (T25), (T26), (T29), (T30), (T35), and (T36)] each X is preferably, independently, hydrogen or halogen, more preferably hydrogen, fluoro, chloro, or bromo, and more preferably still, hydrogen, fluoro or chloro.

Where T contains a Y substituent, [e.g. in (T1), (T2), (T3), (T7), (T8), (T9), (T10), (T11), (T12), (T13), (T14), (T15), (T16), (T17), (T18), (T19), (T20), (T21), (T37), and (T40)] it is preferably hydrogen, $C_1$-$C_3$ alkyl, $C_1$-$C_3$haloalkyl, or halogen. More preferably Y is hydrogen, chloro, fluoro, or bromo.

Where T contains a $R^7$ substituent, [e.g. in (T2), (T3), (T4), (T5), (T6), (T12), (T13), (T14), (T24), and (T28)], which is a substituent borne on a free nitrogen of ring T (by "free nitrogen" it is meant a nitrogen within ring T which is not involved in linking ring T to either group B or to the oxy-alkyl-D moiety), it is preferably hydrogen, $C_1$-$C_3$ alkyl, or $C_1$-$C_3$haloalkyl. Where such an $R^7$ substituent is situated ortho with respect to group B, it is preferably $C_1$-$C_3$ alkyl, or $C_1$-$C_3$haloalkyl, more preferably methyl or halomethyl.

In one set of embodiments, T is (Tp) or is an optionally substituted pyrazolyl ring selected from the group consisting of

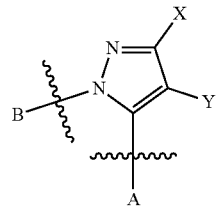 (T1)

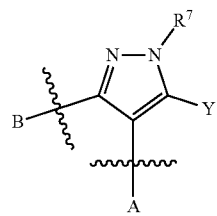 (T2)

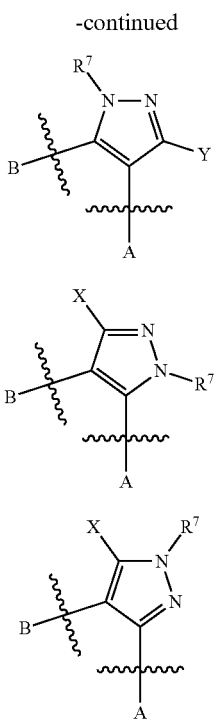

(T3)

(T4)

(T5)

wherein,

X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen;

$R^7$ is hydrogen, $C_1$-$C_3$ alkyl, $C_1$-$C_3$ alkoxy, $C_1$-$C_3$haloalkyl, or $C_1$-$C_3$haloalkoxy, A denotes the point of attachment to the oxy-alkyl-D moiety and B denotes the point of attachment to the pyridazine dione/pyridazinone moiety.

In embodiments where T is an optionally substituted pyrazolyl ring selected from the group consisting of (T1), (T2), (T3), (T4) and (T5), where T contains an X substituent, i.e. in (T1), (T4), and (T5), X is preferably hydrogen or halogen, more preferably hydrogen, fluoro, chloro or bromo, and more preferably still, hydrogen, fluoro or chloro. More preferably in these embodiments, where X is situated ortho with respect to group B (i.e. in T4 and T5) X is preferably halogen, more preferably, fluoro, chloro, or bromo and more preferably still, fluoro, or chloro.

Similarly in such embodiments, where T contains a Y substituent, i.e. in (T1), (T2), and (T3), Y is preferably hydrogen, $C_1$-$C_3$ alkyl, $C_1$-$C_3$haloalkyl, or halogen. More preferably Y is hydrogen, chloro, fluoro, or bromo. Similarly in such embodiments where T contains a $R^7$ substituent, i.e. in (T2), (T3), (T4), and (T5), which is a substituent borne on a free nitrogen of the pyrazolyl ring, $R^7$ is preferably $C_1$-$C_3$ alkyl, or $C_1$-$C_3$haloalkyl, more preferably methyl or halomethyl.

In one set of embodiments it is preferred that T is (T3) or (T4). In certain examples of these embodiments, $R^7$ is $C_1$-$C_3$ alkyl, preferably methyl or ethyl, more preferably methyl; Y is $C_1$-$C_3$ alkyl, preferably methyl or ethyl; and X is halogen, preferably bromo, chloro or fluoro, more preferably chloro.

In a further set of embodiments, T is a 6-membered monocyclic heteroaryl ring system containing 1, 2, or 3 heteroatoms independently selected from nitrogen, oxygen and sulphur, said 6-membered ring system being substituted by one or more radicals selected from $X^1$, $X^2$, $X^3$, $X^4$ and $R^7$.

In such embodiments, T is preferably an optionally substituted pyridyl, pyrimidinyl, pyridazinyl, pyrazinyl, or triazinyl ring, more preferably selected from the group consisting of (T43), (T44), (T45), (T46), (T47), (T48), (T49), (T50), (T51), (T52), (T53), (T54), (T55), (T56), (T57), (T58), (T59), (T60), (T61), and (T62).

In such embodiments, $X^1$ is preferably oxo, $C_1$-$C_3$ alkyl, $C_1$-$C_3$haloalkyl, or halogen, more preferably $C_1$-$C_3$alkyl or halogen, and even more preferably chloro, fluoro, bromo, methyl, or trifluoromethyl. Similarly, $X^2$ and $X^4$ are each independently, preferably hydrogen, oxo, $C_1$-$C_3$alkyl, $C_1$-$C_3$haloalkyl or halogen, more preferably hydrogen or oxo. $X^3$ in such embodiments is preferably hydrogen, $C_1$-$C_3$alkyl, or $C_1$-$C_3$haloalkyl. In such embodiments $R^7$ is preferably hydrogen, $C_1$-$C_3$ alkyl, or $C_1$-$C_3$haloalkyl. Where $R^7$ is ortho with respect to group B, it is more preferably $C_1$-$C_3$ alkyl, or $C_1$-$C_3$haloalkyl.

As described herein, D is a substituted or unsubstituted 5- or 6-membered monocyclic heteroaryl ring containing 1, 2, or 3 heteroatoms independently selected from oxygen, nitrogen and sulphur, and wherein when D is substituted it is substituted on at least one ring carbon atom with $R^3$ and/or on a ring nitrogen atom with $R^9$.

Preferably D is a substituted (as described herein) or unsubstituted furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyridonyl, pyrimidinyl, pyridazinyl, pyrazinyl, 1,2,3-triazinyl, 1,2,4-triazinyl, or 1,3,5-triazinyl ring. For example, D More preferably, D is a substituted or unsubstituted is a substituted or unsubstituted pyrazolyl, imidazolyl, oxazolyl, isoxazolyl, thiazolyl, isothiazolyl, pyridyl, pyridonyl, pyrimidinyl, pyridazinyl, or pyrazinyl ring.

More preferably still, D is a substituted or unsubstituted, oxazolyl, thiazolyl, or, pyridyl, ring.

Preferably each $R^3$ is independently oxo, $C_1$-$C_4$alkyl, $C_1$-$C_4$haloalkyl, halogen, cyano, hydroxyl, $C_1$-$C_4$alkoxy, or $C_1$-$C_4$alkylthio.

Preferably each $R^9$ is independently $C_1$-$C_4$alkyl, $C_1$-$C_4$haloalkyl, hydroxyl, $C_1$-$C_4$alkoxy, or $C_1$-$C_4$alkylthio.

In one preferred set of embodiments, D is selected from the group consisting of 2-pyridyl-, 3-pyridyl-, 4-pyridyl-, 2-thiazolyl-, 4-thiazolyl-, 5-thiazolyl-, pyrazinyl-, 2-pyrimidinyl-, 4-pyrimidinyl-, 5-pyrimidinyl-, 3-pyridazinyl-, 4-pyridazinyl-,

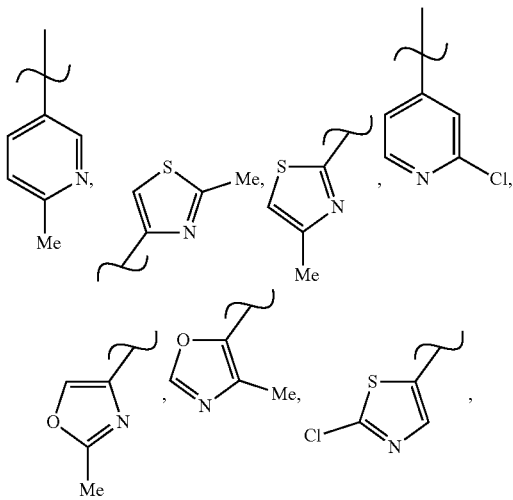

-continued

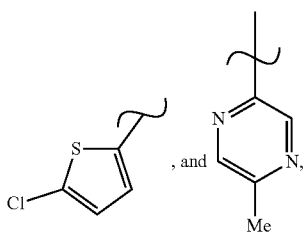, and wherein ~ denotes the point of attachment to the rest of the molecule.

In a further preferred set of embodiments $R^1$ and $R^2$ are each independently methyl or cyclopropyl, G is hydrogen, T is (Tp), $X^{21}$ is chloro or fluoro, $X^{22}$ and $X^{23}$ are both hydrogen, $X^4$ is chloro and D is selected from the group consisting of 2-pyridyl-, 3-pyridyl-, 4-pyridyl-, 2-thiazolyl-, 4-thiazolyl-, 5-thiazolyl-, pyrazinyl-, 2-pyrimidinyl-, 4-pyrimidinyl-, 5-pyrimidinyl-, 3-pyridazinyl-, 4-pyridazinyl-,

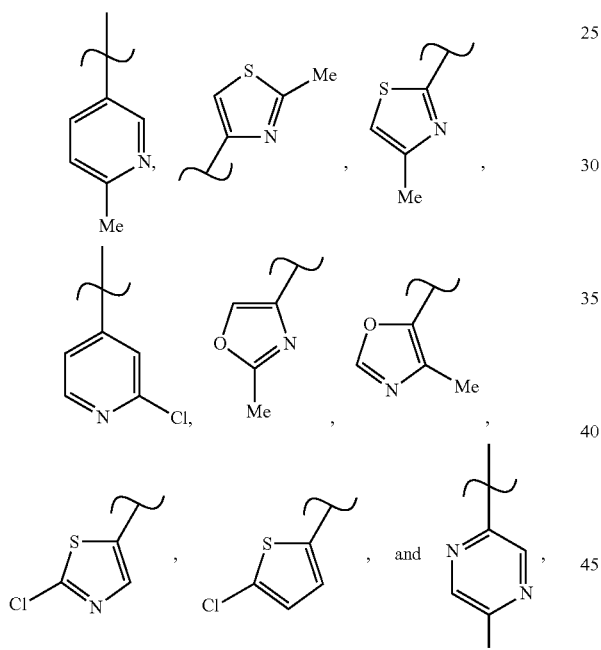

wherein ~ denotes the point of attachment to the rest of the molecule.

In one subset of these preferred embodiments, $R^1$ and $R^2$ are both methyl; in a second subset $R^1$ is methyl and $R^2$ is cyclopropyl; and in a third set $R^1$ is cyclopropyl and $R^2$ is methyl.

In another set of preferred embodiments, D is a substituted or unsubstituted thiazole, a substituted or unsubstituted pyridine, or a substituted or unsubstituted pyrazine, and wherein D is substituted, it is substituted on at least one carbon atom by $R^8$, and each $R^8$ is selected from halogen and $C_1$-$C_3$alkyl (more preferably chloro and methyl).

Tables 1, 2, 3, 4 and 5 below provide 185 specific examples of compounds of formula (I) of the invention.

TABLE 1

Herbicidal compounds of the present invention, wherein the compound of formula (I) has the formula shown below as (I-A), wherein D and $X^{21}$ are as stated in the table

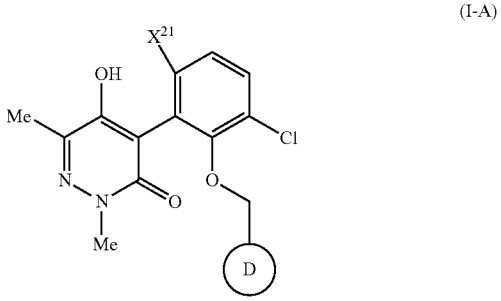

(I-A)

| Compound No. | D | $X^{21}$ |
|---|---|---|
| 1.01 | 2-pyridyl- | Cl |
| 1.02 | 3-pyridyl- | Cl |
| 1.03 | 4-pyridyl- | Cl |
| 1.04 | 2-thiazolyl- | Cl |
| 1.05 | 4-thiazolyl- | Cl |
| 1.06 | 5-thiazolyl- | Cl |
| 1.07 | pyrazinyl- | Cl |
| 1.08 | 2-pyrimidinyl- | Cl |
| 1.09 | 4-pyrimidinyl- | Cl |
| 1.10 | 5-pyrimidinyl- | Cl |
| 1.11 | ![pyridyl-Me structure] | Cl |
| 1.12 | ![thiazolyl-Me structure] | Cl |
| 1.13 | ![thiazolyl-Me structure] | Cl |
| 1.14 | ![pyridyl-Cl structure] | Cl |
| 1.15 | 3-pyridazinyl- | Cl |
| 1.16 | 4-pyridazinyl- | Cl |

TABLE 1-continued

Herbicidal compounds of the present invention, wherein the compound of formula (I) has the formula shown below as (I-A), wherein D and $X^{21}$ are as stated in the table (I-A)

| Compound No. | D | $X^{21}$ |
|---|---|---|
| 1.17 | 2-methyl-oxazol-4-yl | Cl |
| 1.18 | 4-methyl-oxazol-5-yl | Cl |
| 1.19 | 2-chloro-thiazol-5-yl | Cl |
| 1.20 | 5-chloro-thien-2-yl | Cl |
| 1.21 | 5-methyl-pyrazin-2-yl | Cl |
| 1.22 | 2-pyridyl- | F |
| 1.23 | 3-pyridyl- | F |
| 1.24 | 4-pyridyl- | F |
| 1.25 | 2-thiazolyl- | F |
| 1.26 | 4-thiazolyl- | F |
| 1.27 | 5-thiazolyl- | F |
| 1.28 | pyrazinyl- | F |
| 1.29 | 2-pyrimidinyl- | F |
| 1.30 | 4-pyrimidinyl- | F |
| 1.31 | 5-pyrimidinyl- | F |
| 1.32 | 6-methyl-pyridin-3-yl | F |
| 1.33 | 2-methyl-thiazol-4-yl | F |
| 1.34 | 4-methyl-thiazol-2-yl | F |
| 1.35 | 2-chloro-pyridin-4-yl | F |
| 1.36 | 3-pyridazinyl- | F |
| 1.37 | 4-pyridazinyl- | F |
| 1.38 | 2-methyl-oxazol-4-yl | F |
| 1.39 | 4-methyl-oxazol-5-yl | F |

TABLE 1-continued

Herbicidal compounds of the present invention, wherein the compound of formula (I) has the formula shown below as (I-A), wherein D and $X^{21}$ are as stated in the table (I-A)

| Compound No. | D | $X^{21}$ |
|---|---|---|
| 1.40 | 2-chloro-thiazol-5-yl | F |
| 1.41 | 5-chloro-thiophen-2-yl | F |
| 1.42 | 5-methyl-pyrazin-2-yl | F |
| 1.43 | 6-chloro-pyridin-3-yl | Cl |
| 1.44 | 6-chloro-pyridin-3-yl | F |

TABLE 2

Herbicidal compounds of the present invention wherein the compound of formula (I) has the formula shown below as (I-B), wherein D and $X^{21}$ are as stated in the table (I-B)

| Compound No. | D | $X^{21}$ |
|---|---|---|
| 2.01 | 2-pyridyl- | Cl |
| 2.02 | 3-pyridyl- | Cl |
| 2.03 | 4-pyridyl- | Cl |
| 2.04 | 2-thiazolyl- | Cl |
| 2.05 | 4-thiazolyl- | Cl |
| 2.06 | 5-thiazolyl- | Cl |
| 2.07 | pyrazinyl- | Cl |
| 2.08 | 2-pyrimidinyl- | Cl |
| 2.09 | 4-pyrimidinyl- | Cl |
| 2.10 | 5-pyrimidinyl- | Cl |
| 2.11 | 6-methyl-pyridin-3-yl | Cl |
| 2.12 | 2-methyl-thiazol-4-yl | Cl |
| 2.13 | 4-methyl-thiazol-2-yl | Cl |
| 2.14 | 2-chloro-pyridin-4-yl | Cl |
| 2.15 | 3-pyridazinyl- | Cl |
| 2.16 | 4-pyridazinyl- | Cl |

TABLE 2-continued

Herbicidal compounds of the present invention wherein the compound of formula (I) has the formula shown below as (I-B), wherein D and $X^{21}$ are as stated in the table (I-B)

| Compound No. | D | $X^{21}$ |
|---|---|---|
| 2.17 | 2-methyl-oxazol-4-yl | Cl |
| 2.18 | 4-methyl-oxazol-5-yl | Cl |
| 2.19 | 2-chloro-thiazol-5-yl | Cl |
| 2.20 | 5-chloro-thiophen-2-yl | Cl |
| 2.21 | 5-methyl-pyrazin-2-yl | Cl |
| 2.22 | 2-pyridyl- | F |
| 2.23 | 3-pyridyl- | F |
| 2.24 | 4-pyridyl- | F |
| 2.25 | 2-thiazolyl- | F |
| 2.26 | 4-thiazolyl- | F |
| 2.27 | 5-thiazolyl- | F |
| 2.28 | pyrazinyl- | F |
| 2.29 | 2-pyrimidinyl- | F |
| 2.30 | 4-pyrimidinyl- | F |
| 2.31 | 5-pyrimidinyl- | F |
| 2.32 | 6-methyl-pyridin-3-yl | F |
| 2.33 | 2-methyl-thiazol-4-yl | F |
| 2.34 | 4-methyl-thiazol-2-yl | F |
| 2.35 | 2-chloro-pyridin-4-yl | F |
| 2.36 | 3-pyridazinyl- | F |
| 2.37 | 4-pyridazinyl- | F |
| 2.38 | 2-methyl-oxazol-4-yl | F |
| 2.39 | 4-methyl-oxazol-5-yl | F |

TABLE 2-continued

Herbicidal compounds of the present invention wherein the compound of formula (I) has the formula shown below as (I-B), wherein D and $X^{21}$ are as stated in the table (I-B)

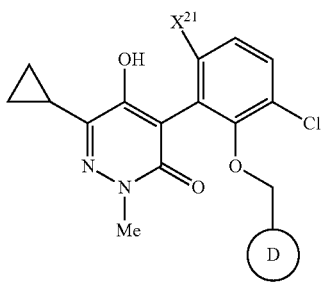

| Compound No. | D | $X^{21}$ |
|---|---|---|
| 2.40 | 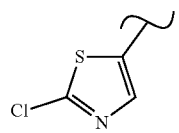 | F |
| 2.41 | 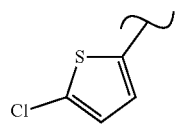 | F |
| 2.42 | 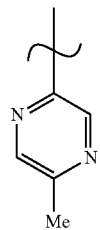 | F |
| 2.43 | 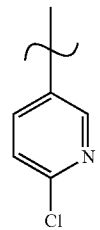 | Cl |
| 2.44 | 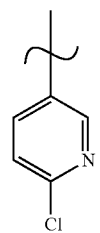 | F |

TABLE 3

Herbicidal compounds of the present invention wherein the compound of formula (I) has the formula shown below as (I-C), wherein D and $X^{21}$ are as stated in the table (I-C)

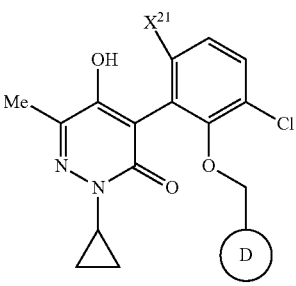

| Compound No. | D | $X^{21}$ |
|---|---|---|
| 3.01 | 2-pyridyl- | Cl |
| 3.02 | 3-pyridyl- | Cl |
| 3.03 | 4-pyridyl- | Cl |
| 3.04 | 2-thiazolyl- | Cl |
| 3.05 | 4-thiazolyl- | Cl |
| 3.06 | 5-thiazolyl- | Cl |
| 3.07 | pyrazinyl- | Cl |
| 3.08 | 2-pyrimidinyl- | Cl |
| 3.09 | 4-pyrimidinyl- | Cl |
| 3.10 | 5-pyrimidinyl- | Cl |
| 3.11 | 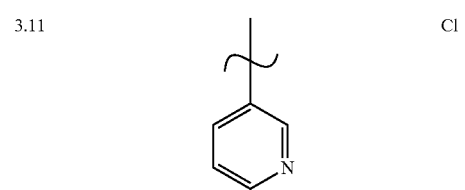 | Cl |
| 3.12 | 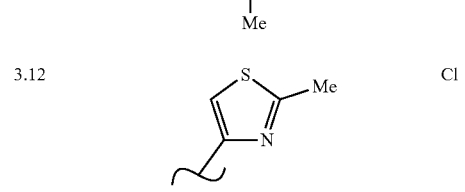 | Cl |
| 3.13 | 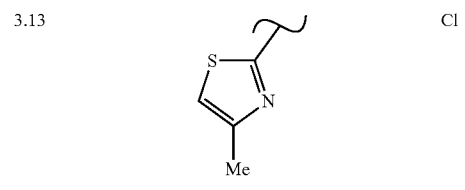 | Cl |
| 3.14 | 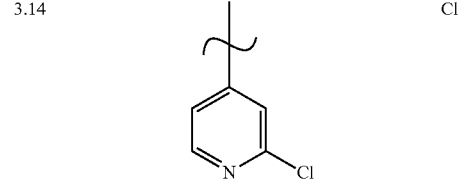 | Cl |
| 3.15 | 3-pyridazinyl- | Cl |
| 3.16 | 4-pyridazinyl- | Cl |

TABLE 3-continued

Herbicidal compounds of the present invention wherein the compound of formula (I) has the formula shown below as (I-C), wherein D and $X^{21}$ are as stated in the table (I-C)

| Compound No. | D | $X^{21}$ |
|---|---|---|
| 3.17 | 2-methyloxazol-4-yl | Cl |
| 3.18 | 4-methyloxazol-5-yl | Cl |
| 3.19 | 2-chlorothiazol-5-yl | Cl |
| 3.20 | 5-chlorothien-2-yl | Cl |
| 3.21 | 5-methylpyrazin-2-yl | Cl |
| 3.22 | 2-pyridyl- | F |
| 3.23 | 3-pyridyl- | F |
| 3.24 | 4-pyridyl- | F |
| 3.25 | 2-thiazolyl- | F |
| 3.26 | 4-thiazolyl- | F |
| 3.27 | 5-thiazolyl- | F |
| 3.28 | pyrazinyl- | F |
| 3.29 | 2-pyrimidinyl- | F |
| 3.30 | 4-pyrimidinyl- | F |
| 3.31 | 5-pyrimidinyl- | F |
| 3.32 | 6-methylpyridin-3-yl | F |
| 3.33 | 2-methylthiazol-4-yl | F |
| 3.34 | 4-methylthiazol-2-yl | F |
| 3.35 | 2-chloropyridin-4-yl | F |
| 3.36 | 3-pyridazinyl- | F |
| 3.37 | 4-pyridazinyl- | F |
| 3.38 | 2-methyloxazol-4-yl | F |
| 3.39 | 4-methyloxazol-5-yl | F |

TABLE 3-continued

Herbicidal compounds of the present invention wherein the compound of formula (I) has the formula shown below as (I-C), wherein D and $X^{21}$ are as stated in the table

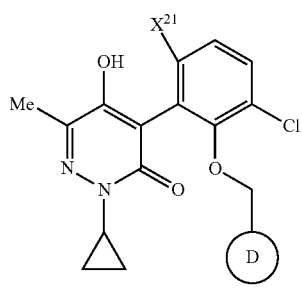

(I-C)

| Compound No. | D | $X^{21}$ |
|---|---|---|
| 3.40 | 2-chloro-thiazol-5-yl | F |
| 3.41 | 5-chloro-thiophen-2-yl | F |
| 3.42 | 5-methyl-pyrazin-2-yl | F |
| 3.43 | 6-chloro-pyridin-3-yl | Cl |
| 3.44 | 6-chloro-pyridin-3-yl | F |

TABLE 4

Herbicidal compounds of the present invention wherein the compound of formula (I) has the formula shown below as (I-D), wherein D and $X^{21}$ are as stated in the table

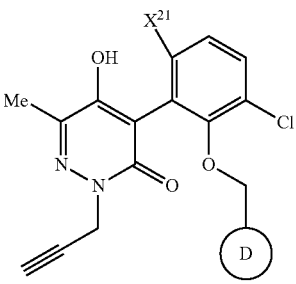

(I-D)

| Compound No. | D | $X^{21}$ |
|---|---|---|
| 4.01 | 2-pyridyl- | Cl |
| 4.02 | 3-pyridyl- | Cl |
| 4.03 | 4-pyridyl- | Cl |
| 4.04 | 2-thiazolyl- | Cl |
| 4.05 | 4-thiazolyl- | Cl |
| 4.06 | 5-thiazolyl- | Cl |
| 4.07 | pyrazinyl- | Cl |
| 4.08 | 2-pyrimidinyl- | Cl |
| 4.09 | 4-pyrimidinyl- | Cl |
| 4.10 | 5-pyrimidinyl- | Cl |
| 4.11 | 6-methyl-pyridin-3-yl | Cl |
| 4.12 | 2-methyl-thiazol-4-yl | Cl |
| 4.13 | 4-methyl-thiazol-2-yl | Cl |
| 4.14 | 2-chloro-pyridin-4-yl | Cl |
| 4.15 | 3-pyridazinyl- | Cl |
| 4.16 | 4-pyridazinyl- | Cl |

TABLE 4-continued

Herbicidal compounds of the present invention wherein the compound of formula (I) has the formula shown below as (I-D), wherein D and $X^{21}$ are as stated in the table (I-D)

| Compound No. | D | $X^{21}$ |
|---|---|---|
| 4.17 | 2-methyl-oxazol-4-yl | Cl |
| 4.18 | 4-methyl-oxazol-5-yl | Cl |
| 4.19 | 2-chloro-thiazol-5-yl | Cl |
| 4.20 | 5-chloro-thiophen-2-yl | Cl |
| 4.21 | 5-methyl-pyrazin-2-yl | Cl |
| 4.22 | 2-pyridyl- | F |
| 4.23 | 3-pyridyl- | F |
| 4.24 | 4-pyridyl- | F |
| 4.25 | 2-thiazolyl- | F |
| 4.26 | 4-thiazolyl- | F |
| 4.27 | 5-thiazolyl- | F |
| 4.28 | pyrazinyl- | F |
| 4.29 | 2-pyrimidinyl- | F |
| 4.30 | 4-pyrimidinyl- | F |
| 4.31 | 5-pyrimidinyl- | F |
| 4.32 | 6-methyl-pyridin-3-yl | F |
| 4.33 | 2-methyl-thiazol-4-yl | F |
| 4.34 | 4-methyl-thiazol-2-yl | F |
| 4.35 | 2-chloro-pyridin-4-yl | F |
| 4.36 | 3-pyridazinyl- | F |
| 4.37 | 4-pyridazinyl- | F |
| 4.38 | 2-methyl-oxazol-4-yl | F |
| 4.39 | 4-methyl-oxazol-5-yl | F |

TABLE 4-continued

Herbicidal compounds of the present invention wherein the compound of formula (I) has the formula shown below as (I-D), wherein D and $X^{21}$ are as stated in the table (I-D)

| Compound No. | D | $X^{21}$ |
|---|---|---|
| 4.40 | 2-Cl-thiazol-5-yl | F |
| 4.41 | 5-Cl-thien-2-yl | F |
| 4.42 | 5-Me-pyrazin-2-yl | F |
| 4.43 | 6-Cl-pyridin-3-yl | Cl |
| 4.44 | 6-Cl-pyridin-3-yl | F |

TABLE 5

Herbicidal compounds of the present invention

| Compound No. | Structural Formula |
|---|---|
| 5.01 | |
| 5.02 | |
| 5.03 | |
| 5.04 | |

TABLE 5-continued

Herbicidal compounds of the present invention

| Compound No. | Structural Formula |
|---|---|
| 5.05 | [structure] |
| 5.06 | [structure] |
| 5.07 | [structure] |
| 5.08 | [structure] |
| 5.09 | [structure] |

In a further set of preferred embodiments T is Tp, $X^{21}$ is halogen, $X^{22}$ is hydrogen or halogen, $X^{23}$ is hydrogen, $X^{24}$ is halogen, $R^1$ is methyl or propargyl, $R^2$ is methyl or halogen, G is hydrogen, and D is 2-pyridyl, 3-pyridyl, 4-pyridyl, 2-thiazolyl, 5-thiazolyl, 2-methyl-4-thiazolyl, 2-chloro-4-thiazolyl, 4-methyl-2-thiazolyl, 2-chloro-4-pyridine, 2-chloro-5-thiophene, or 2-methyl-5-pyrazine; more preferably T is Tp, $X^{21}$ is chloro or fluoro, $X^{22}$ is hydrogen or fluoro, $X^{23}$ is hydrogen, $X^{24}$ is chloro, $R^1$ is methyl or propargyl, $R^2$ is methyl or chloro, G is hydrogen, and D is 2-pyridyl, 3-pyridyl, 4-pyridyl, 2-thiazolyl, 5-thiazolyl, 2-methyl-4-thiazolyl, 2-chloro-4-thiazolyl, 4-methyl-2-thiazolyl, 2-chloro-4-pyridine, 2-chloro-5-thiophene, or 2-methyl-5-pyrazine; most preferably T is Tp, $X^{21}$ is chloro or fluoro, $X^{22}$ is hydrogen or fluoro, $X^{23}$ is hydrogen, $X^{24}$ is chloro, $R^1$ is methyl or propargyl, $R^2$ is methyl, G is hydrogen, and D is 3-pyridyl, 4-pyridyl, 2-thiazolyl, 5-thiazolyl, 2-methyl-4-thiazolyl, 2-chloro-4-thiazolyl, 4-methyl-2-thiazolyl, 2-chloro-4-pyridine, 2-chloro-5-thiophene, or 2-methyl-5-pyrazine.

The compounds of the present invention may be prepared according to the following schemes, in which the substituents $R^1$, $R^2$, $X^{21}$, $X^{22}$, $X^{23}$ and $X^{24}$, and the cyclic moieties T and D, have (unless otherwise stated explicitly) the definitions described herein.

Certain compounds (I-ii) of the present invention may be prepared from compounds of formula (2) as shown in Reaction scheme 1. Compounds (I-ii) are compounds of formula (I) in which G is hydrogen.

Certain compounds (I-iii) of the present invention may be prepared from compounds of formula (21) as shown in Reaction scheme 18. Compounds (I-iii) are compounds of formula (I) in which G is hydrogen and T is a substituted phenyl ring of formula (Tp).

Reaction scheme 1

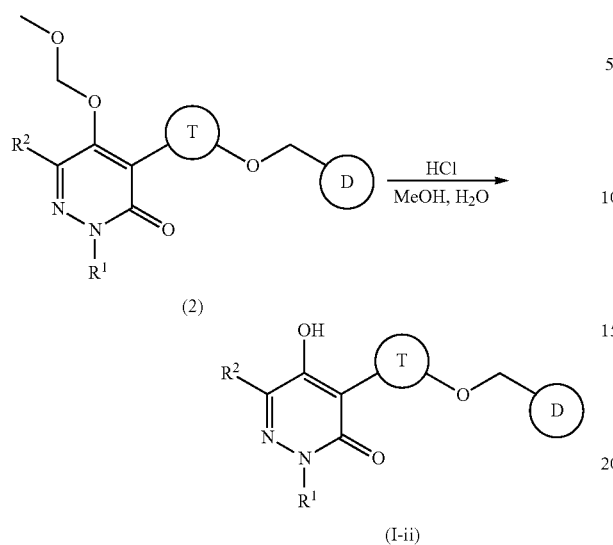

Compounds of formula (I-ii) may be prepared by treatment of compounds of formula (2) with hydrochloric acid in a mixture of water and methanol at a temperature between 0 and 50° C.

Compounds of formula (2) may be prepared from compounds of formula (3) as shown in Reaction scheme 2.

Reaction scheme 2

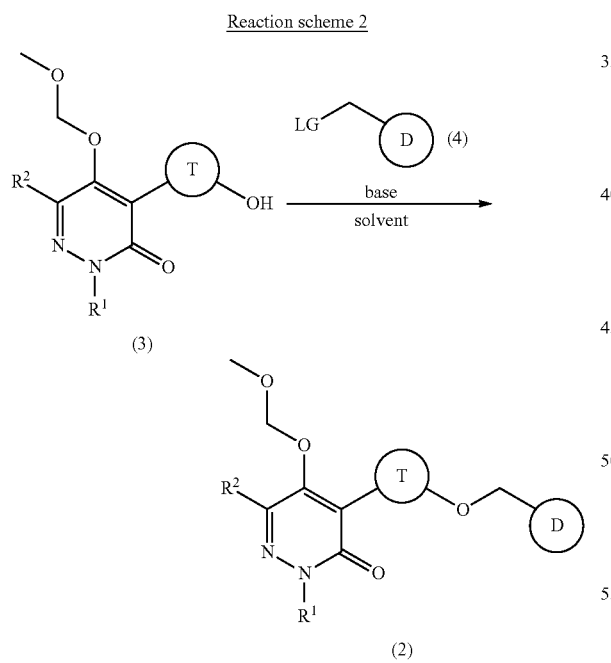

Compounds of formula (2) may be prepared by treatment of compounds (3) with electrophiles (4) [wherein LG is a leaving group such as a halide (for example chloride, bromide or iodide) or a sulfonate (for example mesylate or tosylate)] in the presence of a suitable base and solvent at a temperature between 0 and 70° C. Examples of suitable bases are potassium carbonate and sodium hydride. Examples of suitable solvents are acetone and N,N-dimethylformamide. Many electrophiles (4), or their salts, are commercially available [such as 2-(bromomethyl)pyridine hydrobromide and 2-chloro-5-chloromethylthiazole].

Compounds (3) may be prepared from compounds (5) as shown in Reaction scheme 3.

Reaction scheme 3

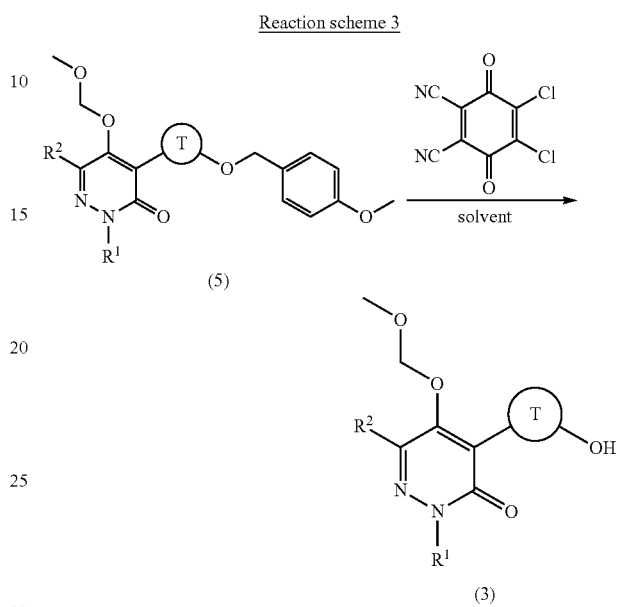

Compounds of formula (3) may be prepared by treatment of compounds (5) with 2,3-dichloro-5,6-dicyano-p-benzoquinone (DDQ) in a solvent [such as dichloromethane or aqueous acetonitrile] at a temperature between 0 and 50° C.

Compounds (5) may be prepared from compounds (6) as shown in Reaction scheme 4.

Reaction scheme 4

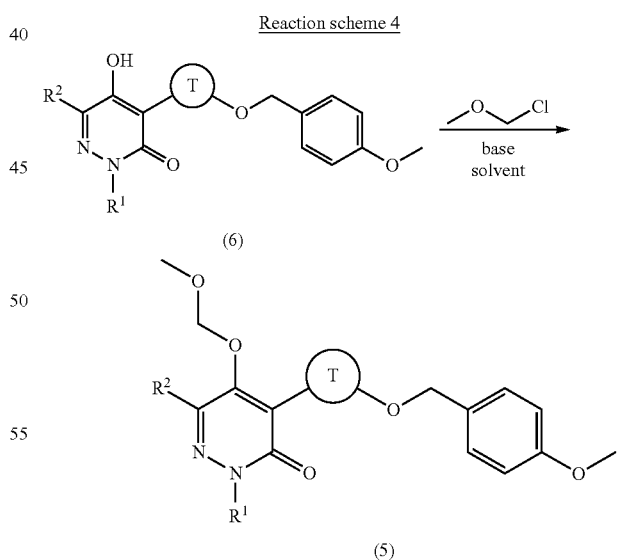

Compounds of formula (5) may be prepared by treatment of compounds (6) with chloromethyl methyl ether in the presence of a suitable base and solvent, at a temperature between 0 and 40° C. Examples of suitable bases are sodium hydride and triethylamine. Examples of suitable solvents are dichloromethane and N,N-dimethylformamide.

Compounds (6) may be prepared from compounds (7) as shown in Reaction scheme 5.

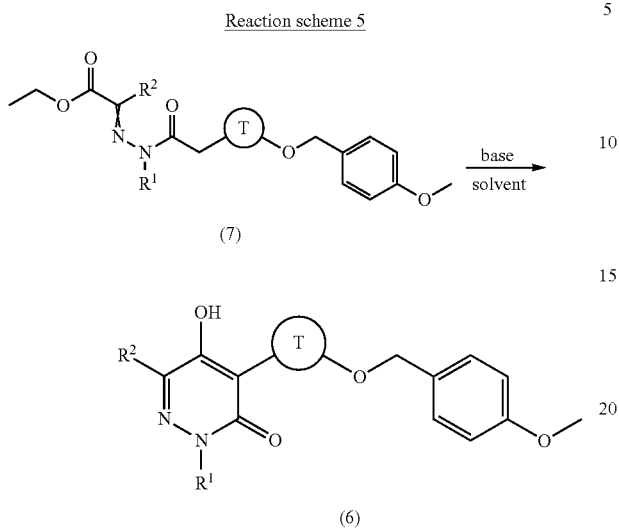

Compounds of formula (6) may be prepared by treatment of ester compounds (7) with a suitable base, in a suitable solvent, at a temperature between 100 and 150° C. Microwave heating or conventional heating may be used. Examples of suitable bases are 1,8-diazabicyclo[5.4.0]undec-7-ene (DBU) and sodium hydride. Examples of suitable solvents are acetonitrile, N,N-dimethylformamide and toluene.

Compounds (7) may be prepared from compounds of formulae (8) and (9) as shown in Reaction scheme 6 or from compounds of formulae (10) and (20) as shown in Reaction scheme 16.

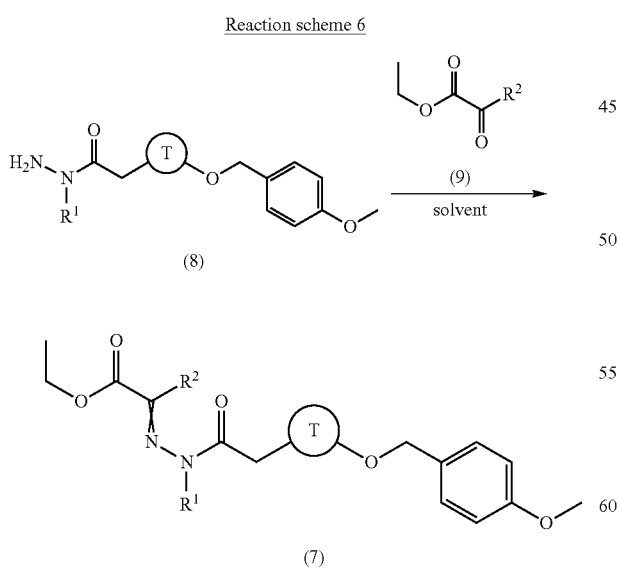

Compounds of formula (7) may be prepared by condensation of compounds (8) with α-keto esters (9) in the presence of a suitable solvent, at a temperature between 50 and 100° C. Examples of suitable solvents are methanol and ethanol. With reference to Reaction scheme 6, many α-keto esters (9) are commercially available. Examples are ethyl pyruvate and ethyl 3-methyl-2-oxobutyrate.

Compounds of formula (8) may be prepared from compounds of formulae (10) and (11) as shown in Reaction scheme 7.

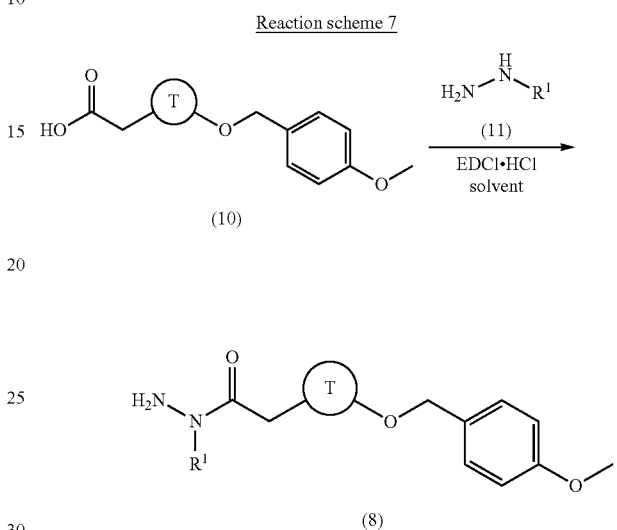

Compounds of formula (8) may be prepared by reaction of compounds of formula (10) and alkylhydrazines (11) in the presence of N-(3-Dimethylaminopropyl)-N'-ethylcarbodiimide hydrochloride (EDCl.HCl) and a solvent, at a temperature between 0 and 40° C. Examples of suitable solvents are dichloromethane and N,N-dimethylformamide. With reference to Reaction scheme 7, many alkylhydrazines (11) are commercially available. Examples are methylhydrazine and ethylhydrazine.

Compounds of formula (10-i) are compounds of formula (10) in which T is a substituted phenyl ring of formula (Tp). Compounds (10-i) may be prepared from compounds (12) as shown in Reaction scheme 8.

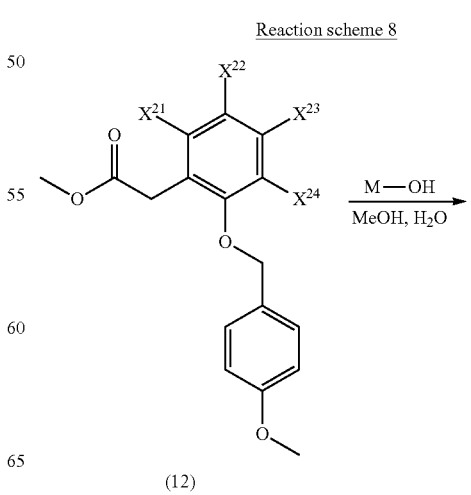

-continued

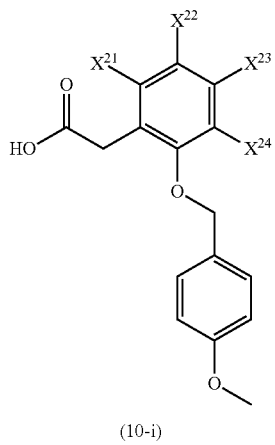

(10-i)

Compounds of formula (10-i) may be prepared by hydrolysis of compounds of formula (12) with an alkali metal hydroxide in a mixture of methanol and water at a temperature between 20 and 100° C. Examples of suitable alkali metal hydroxides are sodium hydroxide and potassium hydroxide.

Compounds of formula (12) may be prepared from compounds (13) as shown in Reaction scheme 9.

Reaction scheme 9

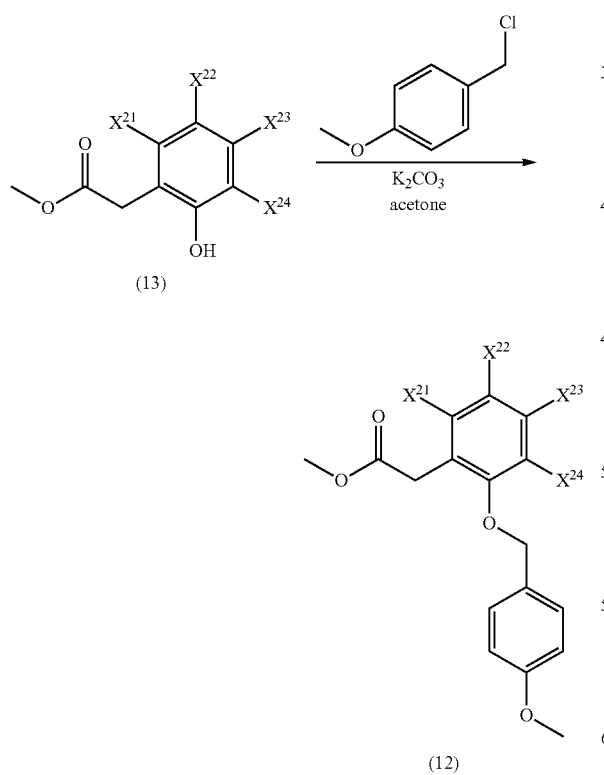

(13)

(12)

Compounds of formula (12) may be prepared by alkylation of compounds of formula (13) with 4-methoxybenzyl chloride in the presence of potassium carbonate in acetone at a temperature between 20 and 70° C.

Compounds of formula (13) may be prepared from compounds (14) as shown in Reaction scheme 10.

Reaction scheme 10

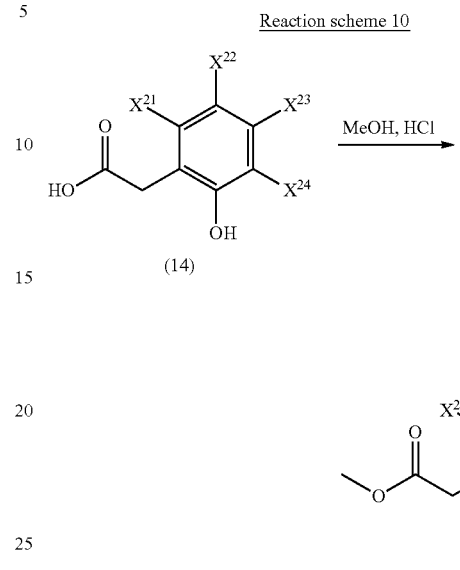

(14)

(13)

Compounds of formula (13) may be prepared by esterification of compounds (14) with methanol in the presence of an acid [such as hydrochloric acid or sulfuric acid] at a temperature between 20 and 100° C.

With reference to Reaction scheme 10, an example of compounds (14) is 2-(3,6-dichloro-2-hydroxy-phenyl)acetic acid, prepared according to *Analytical Biochemistry*, 1966, 16, 253. Other compounds (14) may be synthesised similarly, according to Reaction scheme 11.

Reaction scheme 11

(15)

(14)

Compounds of formula (14) may be prepared by treatment of compounds (15) with hydrobromic acid in water at a temperature between 20 and 100° C.

Compounds of formula (15) may be prepared from compounds (16) as shown in Reaction scheme 12.

Reaction scheme 12

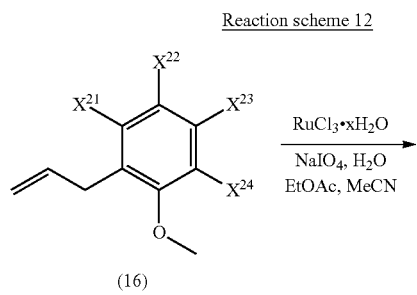

(16)

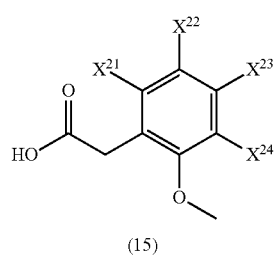

(15)

Compounds of formula (15) may be prepared by treatment of compounds (16) with ruthenium tetroxide, generated in situ from ruthenium trichloride hydrate and sodium metaperiodate, in a mixture of water, ethyl acetate and acetonitrile at a temperature between 0 and 40° C.

Compounds of formula (16) may be prepared from compounds (17) as shown in Reaction scheme 13.

Reaction scheme 13

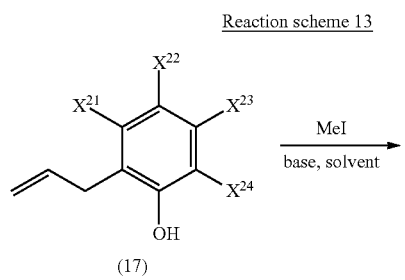

(17)

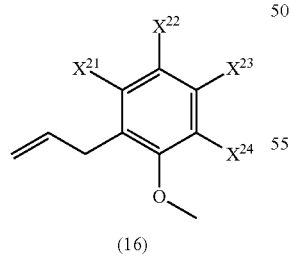

(16)

Compounds of formula (16) may be prepared by treatment of compounds (17) with methyl iodide in the presence of a suitable base and solvent at a temperature between 20 and 70° C. Examples of suitable bases are potassium carbonate and sodium hydroxide. Examples of suitable solvents are acetone and N,N-dimethylformamide.

Compounds of formula (17) may be prepared as shown in Reaction scheme 14.

Reaction scheme 14

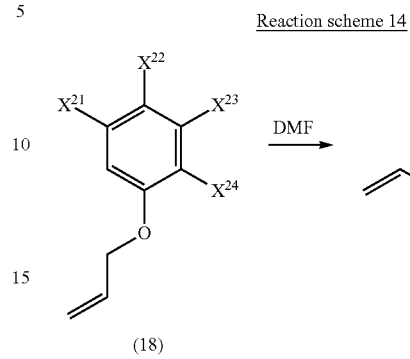

(18)         (17)

Compounds (17) may be prepared by heating compounds (18) in the presence of N,N-dimethylformamide, at a temperature between 180 and 220° C.

With reference to Reaction scheme 14, an example of compounds (18) is 2-allyloxy-1,4-dichloro-benzene, prepared according to *J. Chem. Soc., Perkin Trans.* 2, 2001, 1824. Other compounds (18) may be synthesised similarly, according to Reaction scheme 15.

Reaction scheme 15

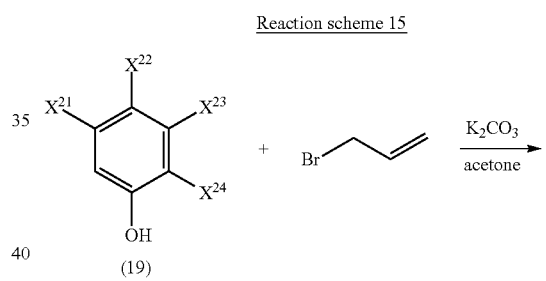

(19)

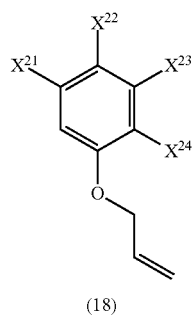

(18)

Compounds (18) may be prepared by treatment of compounds (19) with allyl bromide in the presence of potassium carbonate and acetone, at a temperature between 20 and 70° C.

With reference to Reaction scheme 15, many phenol compounds (19) are commercially available. Examples are 2,5-dichlorophenol and 2-chloro-5-fluorophenol.

Reaction scheme 16

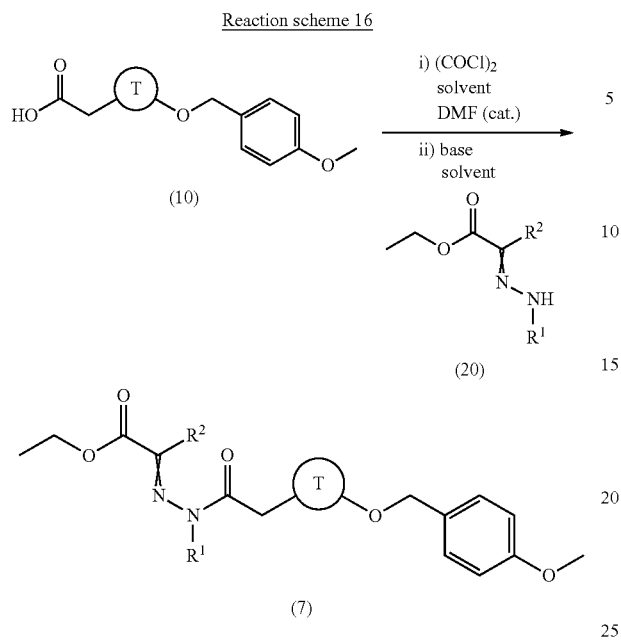

Compounds of formula (7) may be prepared by N-acylation of hydrazones (20) with the acyl chloride derivative of compounds (10), in the presence of a suitable base and solvent, at a temperature between 0 and 25° C. The acyl chloride is pre-formed by treatment of compounds of formula (10) with oxalyl chloride in a suitable solvent, optionally with inclusion of N,N-dimethylformamide as a catalyst, at a temperature between 0 and 50° C. Examples of suitable bases are triethylamine and pyridine. Examples of suitable solvents are dichloromethane and chloroform. Compounds of formula (20) may be prepared from alkylhydrazines (11) and α-keto esters (9) as shown in Reaction scheme 17.

Reaction scheme 17

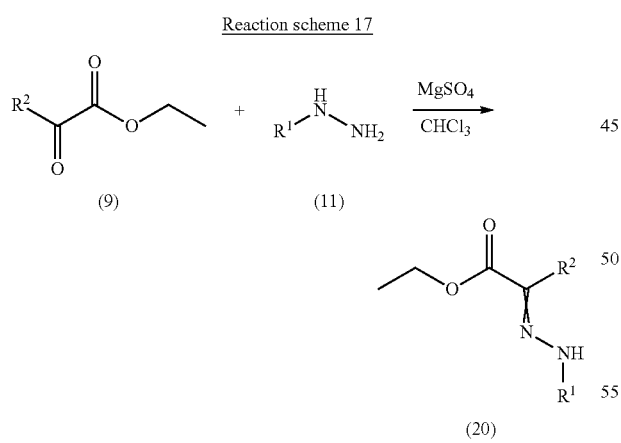

Compounds (20) may be prepared from alkylhydrazines (11) and α-keto esters (9) in the presence of MgSO$_4$ and chloroform, at a temperature between 0 and 40° C. With reference to Reaction scheme 17, many alkylhydrazines (11) are commercially available. Examples are methylhydrazine and ethylhydrazine. With reference to Reaction scheme 17, many α-keto esters (9) are commercially available. Examples are ethyl pyruvate and ethyl 3-methyl-2-oxobutyrate.

Reaction scheme 18

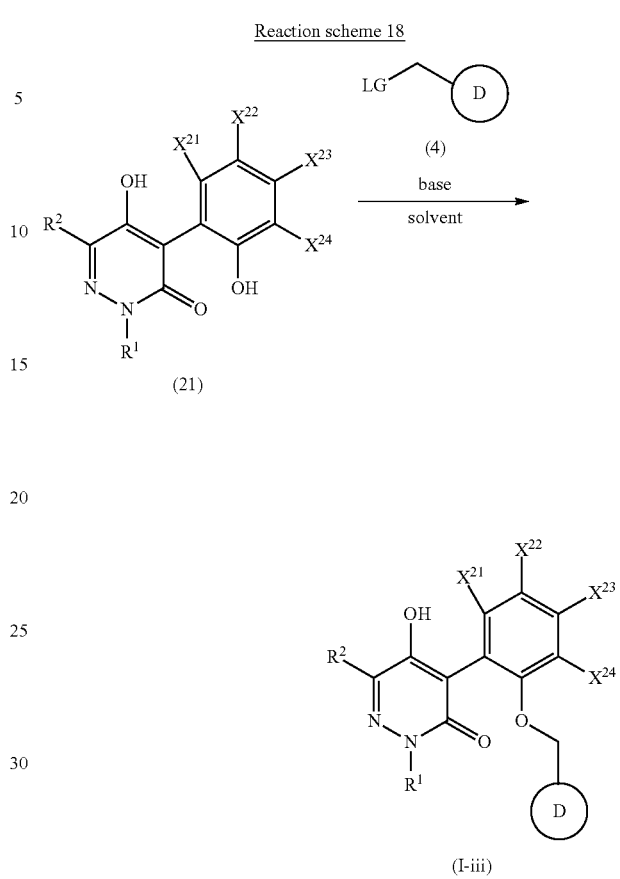

Compounds (I-iii) may be prepared by alkylation of compounds of formula (21) with electrophiles (4) [wherein LG is a leaving group such as a halide (for example chloride, bromide or iodide) or a sulfonate (for example mesylate or tosylate)] in the presence of a suitable base and solvent at a temperature between −50 and 70° C. Examples of suitable bases are sodium hexamethyldisilazide, potassium hexamethyldisilazide and sodium hydride. Examples of suitable solvents are tetrahydrofuran, 2-methyl tetrahydrofuran and N,N-dimethylformamide. Many electrophiles (4), or their salts, are commercially available [such as 2-(bromomethyl)pyridine hydrobromide and 2-chloro-5-chloromethylthiazole]. Compounds of formula (21) are made according to Reaction scheme 19.

Reaction scheme 19

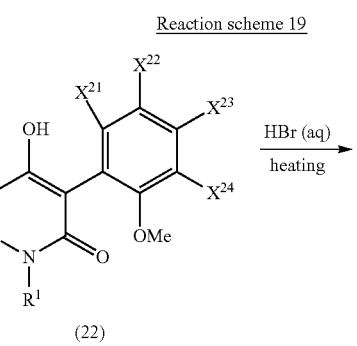

-continued

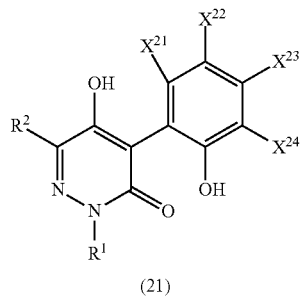

(21)

Compounds of formula (21) may be prepared by heating compounds (22) in hydrobromic acid at reflux. Compounds (22) are made according to Reaction scheme 20.

Reaction scheme 20

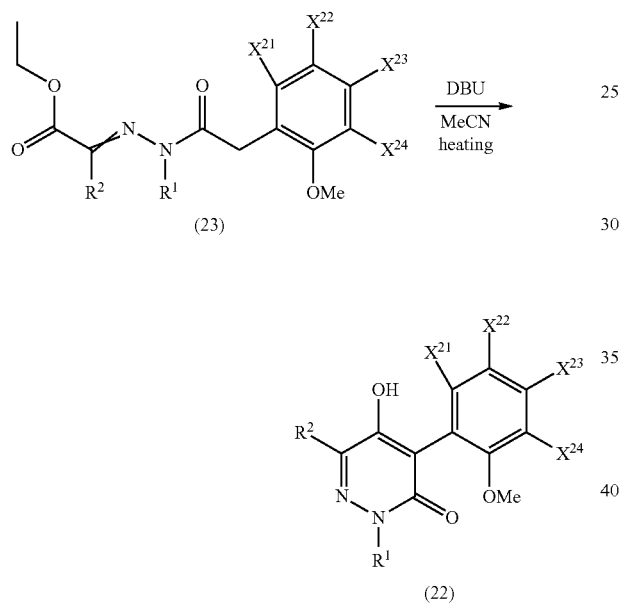

Compounds of formula (22) may be prepared by heating hydrazones of formula (23) with 1,8-Diazabicyclo[5.4.0]undec-7-ene [DBU] in acetonitrile at a temperature between 50° C. and 150° C. Hydrazones (23) are made according to Reaction scheme 21.

Reaction scheme 21

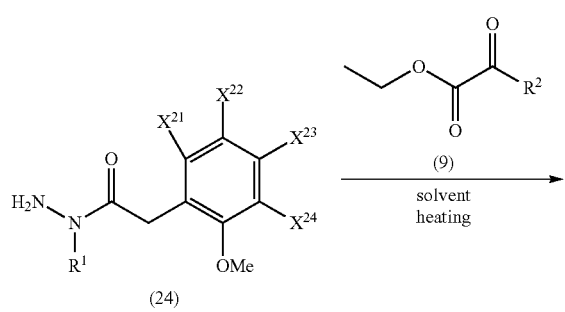

-continued

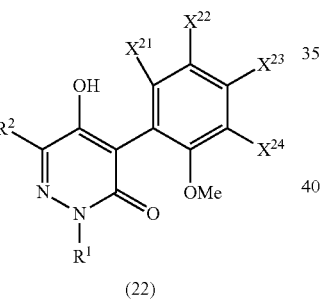

(23)

Hydrazones of formula (23) may be prepared by heating compounds of formula (24) with α-keto esters (9) in a solvent [such as methanol or ethanol] at a temperature between 25° C. and 100° C. With reference to Reaction scheme 21, many α-keto esters (9) are commercially available. Examples are ethyl pyruvate and ethyl 3-methyl-2-oxobutyrate. Compounds of formula (24) are made according to Reaction scheme 22.

Reaction scheme 22

Compounds of formula (24) may be prepared by reacting compounds of formula (15) with alkylhydrazines (11) in the presence of EDC hydrochloride [N-(3-dimethylaminopropyl)-N'-ethylcarbodiimide hydrochloride, CAS number: 25952-53-8] in a solvent [such as dichloromethane, tetrahydrofuran or acetonitrile] at a temperature between 0° C. and 60° C. A base may optionally be included [such as triethylamine or diisopropylethylamine]. Compounds of formula (15) are made according to Reaction Scheme 12. With reference to Reaction scheme 22, many alkylhydrazines (11) are commercially available. Examples are methylhydrazine and ethylhydrazine.

The skilled man will appreciate that certain intermediates described herein are also novel, and as such these form further aspects of the invention.

The compounds according to the invention can be used as herbicidal agents in unmodified form, but they are generally formulated into compositions in various ways using formulation adjuvants, such as carriers, solvents and surface-active substances.

The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance. The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following Examples further illustrate, but do not limit, the invention:

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |

| Suspension concentrate | |
| --- | --- |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

The composition of the present may further comprise at least one additional pesticide. For example, the compounds according to the invention can also be used in combination with other herbicides or plant growth regulators. In a preferred embodiment the additional pesticide is a herbicide and/or herbicide safener.

Thus, compounds of formula (I) can be used in combination with one or more other herbicides to provide various herbicidal mixtures. Specific examples of such mixtures include (wherein "I" represents a compound of formula (I)):—I+acetochlor; I+acifluorfen-sodium; I+aclonifen; I+alachlor; I+alloxydim; I+ametryn; I+amicarbazone; I+amidosulfuron; I+aminocyclopyrachlor; I+aminopyralid; I+amitrole; I+asulam; I+atrazine; I+bensulfuron-methyl; I+bentazone; I+bicyclopyrone; I+bifenox; I+bispyribac-sodium; I+bromacil; I+bromoxynil; I+butafenacil; I+cafens- trole; I+carfentrazone-ethyl; I+chlorimuron-ethyl; I+chlorotoluron; I+cinosulfuron; I+clethodim; I+clodinafop-propargyl; I+clomazone; I+clopyralid; I+cyhalofop-butyl; I+2,4-D (including the choline salt and 2-ethylhexyl ester thereof); I+daimuron; I+desmedipham; I+dicamba (including the aluminum, aminopropyl, bis-aminopropylmethyl, choline, diglycolamine, dimethylamine, dimethylammonium, potassium and sodium salts thereof); I+diclofop-methyl; I+difenzoquat; I+diflufenican; I+diflufenzopyr; I+dimethachlor; I+dimethenamid-P; I+diquat dibromide; I+diuron; I+esprocarb; I+ethofumesate; I+fenoxaprop-P-ethyl; I+fenquinotrione; I+flazasulfuron; I+florasulam; I+fluazifop-P-butyl; I+flucarbazone-sodium; I+flufenacet; I+flumetralin; I+flumetsulam; I+flumioxazin; I+flupyrsulfuron-methyl-sodium; I+fluroxypyr-meptyl; I+fluthiacet-methyl; I+fomesafen; I+foramsulfuron; I+glufosinate (including the ammonium salt thereof); I+glyphosate (including the diammonium, isopropylammonium and potassium salts thereof); I+halauxifen-methyl; I+halosulfuron-methyl; I+haloxyfop-methyl; I+hexazinone; I+imazamox; I+imazapic; I+imazapyr; I+imazaquin; I+imazethapyr; I+indaziflam; I+iodosulfuron-methyl-sodium; I+iofensulfuron; I+iofensulfuron-sodium; I+ioxynil; I+ipfencarbazone; I+isoxaben; I+isoxaflutole; I+lactofen; I+linuron; I+mecoprop-P; I+mefenacet; I+mesosulfuron; I+mesosulfuron-methyl; I+mesotrione; I+metamitron; I+metobromuron; I+metolachlor; I+metoxuron; I+metribuzin; I+metsulfuron; I+molinate; I+napropamide; I+nicosulfuron; I+norflurazon; I+orthosulfamuron; I+oxadiargyl; I+oxadiazon; I+oxyfluorfen; I+paraquat dichloride; I+pendimethalin; I+penoxsulam; I+phenmedipham; I+picloram; I+picolinafen; I+pinoxaden; I+pretilachlor; I+primisulfuron-methyl; I+prodiamine; I+prometryn; I+propachlor; I+propanil; I+propaquizafop; I+propham; I+propyzamide; I+prosulfocarb; I+prosulfuron; I+pyrasulfotole; I+pyrazolynate, I+pyrazosulfuron-ethyl; I+pyribenzoxim; I+pyridate; I+pyriftalid; I+pyrithiobac-sodium; I+pyroxasulfone; I+pyroxsulam; I+quinclorac; I+quizalofop-P-ethyl; I+rimsulfuron; I+saflufenacil; I+sethoxydim; I+S-metolachlor; I+sulcotrione; I+sulfentrazone; I+tebuthiuron; I+tefuryltrione; I+tembotrione; I+terbuthylazine; I+terbutryn; I+thiencarbazone; I+thifensulfuron; I+tiafenacil; I+tolpyralate; I+topramezone; I+tralkoxydim; I+triafamone; I+triasulfuron; I+tribenuron-methyl; I+triclopyr; I+trifloxysulfuron-sodium; I+trifludimoxazin and tritosulfuron.

Especially preferred examples of such mixtures include:—I+ametryn; I+atrazine; I+bicyclopyrone; I+butafenacil; I+chlorotoluron; I+clodinafop-propargyl; I+clomazone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+dimethachlor; I+diquat dibromide; I+fluazifop-P-butyl; I+flumetralin; I+fomesafen;

I+glufosinate-ammonium; I+glyphosate (including the diammonium, isopropylammonium and potassium salts thereof); I+mesotrione; I+molinate; I+napropamide; I+nicosulfuron; I+paraquat dichloride; I+pinoxaden; I+pretilachlor; I+primisulfuron-methyl; I+prometryn; I+prosulfocarb; I+prosulfuron; I+pyridate; I+pyriftalid; I+pyrazolynate, I+S-metolachlor; I+terbuthylazine; I+terbutryn; I+tralkoxydim; I+triasulfuron and I+trifloxysulfuron-sodium.

Preferred herbicide mixture products for weed control in cereals (especially wheat and/or barley) include:—I+amidosulfuron; I+aminopyralid; I+bromoxynil; I+carfentrazone-ethyl; I+chlorotoluron; I+clodinafop-propargyl; I+clopyralid; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+difenzoquat; I+diflufenican; I+fenoxaprop-P-ethyl; I+florasulam; I+flucarbazone-sodium; I+flufenacet; flupyrsulfuron-methyl-sodium; I+fluroxypyr-meptyl; I+halauxifen-methyl; I+iodosulfuron-methyl-sodium; I+iofensulfuron; I+iofensulfuron-sodium; I+mesosulfuron; I+mesosulfuron-methyl; I+metsulfuron; I+pendimethalin; I+pinoxaden; I+prosulfocarb; I+pyrasulfotole; I+pyroxasulfone; I+pyroxsulam; I+topramezone; I+tralkoxydim; I+triasulfuron and I+tribenuron-methyl.

Preferred herbicide mixture products for weed control in corn include:—I+acetochlor; I+alachlor; I+atrazine; I+bicyclopyrone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+diflufenzopyr; I+dimethenamid-P; I+flumioxazin; I+fluthiacet-methyl; I+foramsulfuron; I+glufosinate (including the ammonium salt thereof); I+glyphosate (including the diammonium, isopropylammonium and potassium salts thereof); I+isoxaflutole; I+mesotrione; I+nicosulfuron; I+primisulfuron-methyl; I+prosulfuron; I+pyroxasulfone; I+rimsulfuron; I+S-metolachlor, I+terbutylazine; I+tembotrione; I+thiencarbazone and I+thifensulfuron.

Preferred herbicide mixture products for weed control in rice include:—I+2,4-D; I+2,4-D choline salt; I+2,4-D-2-ethylhexyl ester; I+bensulfuron-methyl; I+bispyribac-sodium; I+cafenstrole; I+cinosulfuron; I+clomazone; I+cyhalofop-butyl; I+daimuron; I+dicamba (including the aluminum, aminopropyl, bis-aminopropylmethyl, choline, diglycolamine, dimethylamine, dimethylammonium, potassium and sodium salts thereof); I+esprocarb; I+fenoxaprop-P-ethyl; I+florasulam; I+halauxifen-methyl; I+halosulfuron-methyl; I+iofensulfuron; I+ipfencarbazone; I+mefenacet; I+mesotrione; I+metsulfuron; I+molinate; I+orthosulfamuron; I+oxadiargyl; I+oxadiazon; I+pendimethalin; I+penoxsulam; I+pretilachlor; I+pyrazolynate, I+pyrazosulfuron-ethyl; I+pyribenzoxim; I+pyriftalid; I+quinclorac; I+tefuryltrione; I+triafamone and I+triasulfuron.

Preferred herbicide mixtures for weed control in soybean include:—I+acifluorfen-sodium; I+ametryn; I+atrazine; I+bentazone; I+bicyclopyrone; I+bromoxynil; I+carfentrazone-ethyl; I+chlorimuron-ethyl; I+clethodim; I+clomazone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+diquat dibromide; I+diuron; I+fenoxaprop-P-ethyl; I+fluazifop-P-butyl; I+flufenacet; I+flumioxazin; I+fomesafen; I+glufosinate (including the ammonium salt thereof); I+glyphosate (including the diammonium, isopropylammonium and potassium salts thereof); I+imazethapyr; I+lactofen; I+mesotrione; I+metolachlor; I+metribuzin; I+nicosulfuron; I+oxyfluorfen; I+paraquat dichloride; I+pendimethalin; I+pyroxasulfone; I+quizalofop-P-ethyl; I+saflufenacil; I+sethoxydim; I+S-metolachlor and I+sulfentrazone.

The mixing partners of the compound of Formula (I) may also be in the form of esters or salts, as mentioned e.g. in The Pesticide Manual, Fourteenth Edition, British Crop Protection Council, 2006.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

Compounds of formula (I) of the present invention may also be combined with herbicide safeners. Preferred combinations (wherein "I" represents a compound of Formula (I)) include:—I+benoxacor, I+cloquintocet-mexyl; I+cyprosulfamide; I+dichlormid; I+fenchlorazole-ethyl; I+fenclorim; I+fluxofenim; I+furilazole I+isoxadifen-ethyl; I+mefenpyr-diethyl; I+N-(2-methoxybenzoyl)-4-[(methylaminocarbonyl)amino] benzenesulfonamide and I+oxabetrinil.

Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of formula (I) may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

The compounds of formula (I) of this invention are useful as herbicides. The present invention therefore further comprises a method for controlling unwanted plants comprising applying to the said plants or a locus comprising them, an effective amount of a compound of the invention or a herbicidal composition containing said compound. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula (I) according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. In a particularly preferred aspect, the crop plant has been engineered to overexpress homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Compounds of formula I and compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*. Weeds can also include plants which may be considered crop plants but which are growing outside a crop area (escapes), or which grow from seed left over from a previous planting of a different crop (volunteers). Such volunteers or escapes may be tolerant to certain other herbicides.

Various aspects and embodiments of the present invention will now be illustrated in more detail by way of example. It will be appreciated that modification of detail may be made without departing from the scope of the invention.

PREPARATION EXAMPLES

Example 1 Preparation of 4-[3,6-dichloro-2-(2-pyridylmethoxy)phenyl]-2,6-dimethyl-pyridazine-3,5-dione, trifluoroacetic acid salt

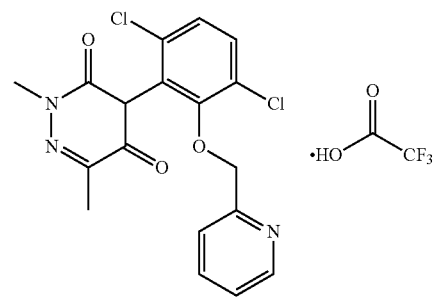

1.1 2-Allyl-3,6-dichloro-phenol

A mixture of 2-allyloxy-1,4-dichloro-benzene (1.0 g, 4.9 mmol, 1.0 eq.) and N,N-dimethylformamide (0.1 mL) was heated at an external temperature of 220° C. for 1 hour. The mixture was allowed to cool to room temperature and was concentrated in vacuo to provide 2-allyl-3,6-dichloro-phenol as a brown oil (0.99 g, 99%).

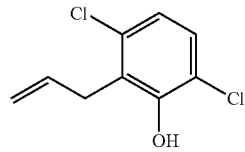

$^1$H NMR (400 MHz, CDCl$_3$): δ$_H$: 7.18-7.08 (1H, m) 6.95-6.85 (1H, m) 6.02-5.84 (1H, m) 5.71 (1H, s) 5.14-4.99 (2H, m) 3.59 (2H, dt).

1.2 2-Allyl-1,4-dichloro-3-methoxy-benzene

Iodomethane (12.9 mL, 207 mmol) was added to a suspension of 2-allyl-3,6-dichloro-phenol (40.0 g, 197 mmol) and potassium carbonate (30.2 g, 217 mmol) in acetone (490 mL) and the mixture was stirred at room temperature for 24 hours. The mixture was filtered and the filtrate was concentrated in vacuo. The residue was dissolved in a mixture of diethyl ether (150 mL) and water (150 mL) then separated. The organic extracts were dried over MgSO$_4$, passed through a hydrophobic frit and concentrated in vacuo to provide 2-allyl-1,4-dichloro-3-methoxy-benzene (38.0 g, 89%) as an orange oil.

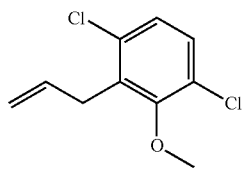

$^1$H NMR (400 MHz, CDCl$_3$): δ$_H$: 7.23-7.17 (m, 1H), 7.14-7.07 (m, 1H), 6.03-5.90 (m, 1H), 5.12-4.96 (m, 2H), 3.86 (s, 3H), 3.58 (td, 2H).

1.3 2-(3,6-Dichloro-2-methoxy-phenyl)acetic acid

Ruthenium(III) chloride hydrate (0.355 g, 1.71 mmol) was added to a solution of 2-allyl-1,4-dichloro-3-methoxy-benzene (18.6 g, 85.7 mmol) in a mixture of water (250 mL), acetonitrile (170 mL) and ethyl acetate (170 mL). Sodium metaperiodate (91.8 g, 428 mmol) was added portion wise over a period of 30 minutes. The mixture was stirred for 10 minutes then cooled to 5° C. The mixture was quenched by the addition of an aqueous solution of sodium metabisulfite (0.65 g/g) over 2 hours. The mixture was diluted with brine (200 mL) then separated. The aqueous layer was extracted with ethyl acetate (3×200 mL). The combined organic extracts were dried over MgSO$_4$, filtered and concentrated in vacuo. The crude product was purified by flash column chromatography to provide 2-(3,6-dichloro-2-methoxy-phenyl)acetic acid (11.9 g, 59%) as a white solid.

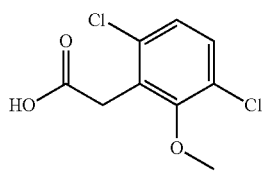

$^1$H NMR (400 MHz, CDCl$_3$): δ$_H$: 7.28 (d, 1H), 7.14 (d, 1H), 3.93 (s, 2H), 3.88 (s, 3H).

1.4 2-(3,6-Dichloro-2-hydroxy-phenyl)acetic acid 2-(3,6-Dichloro-2-methoxy-phenyl)acetic acid (11.8 g, 50.2 mmol) was added to hydrobromic acid (48% aqueous solution) (100 mL, 887 mmol) and the mixture was heated at reflux for 9 hours. The mixture was allowed to cool to room temperature. The mixture was filtered and the filtrand was dissolved in a 1:1 mixture of dichloromethane and ethyl acetate (200 mL). The mixture was dried over MgSO$_4$, passed through a hydrophobic frit and concentrated in vacuo to provide 2-(3,6-dichloro-2-hydroxy-phenyl)acetic acid (10.2 g, 92%) as a yellow solid.

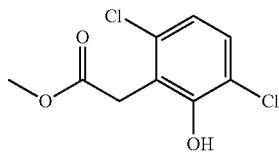

$^1$H NMR (400 MHz, CDCl$_3$): δ$_H$: 12.45 (br. s., 1H), 9.91 (br. s., 1H), 7.31 (d, 1H), 6.97 (d, 1H), 3.72 (s, 2H).

1.5 Methyl 2-(3,6-dichloro-2-hydroxy-phenyl)acetate

Sulfuric acid (4.5 mL) was added to a solution of 2-(3,6-dichloro-2-hydroxy-phenyl)acetic acid (10.1 g, 45.7 mmol) in methanol (45 mL) and the mixture was heated at reflux for 1 hour. The mixture was allowed to cool to room temperature and was diluted with water (100 mL). The mixture was extracted with dichloromethane (3×100 mL) and the combined organic extracts were dried over MgSO$_4$, passed through a hydrophobic frit and concentrated in vacuo. The crude product was purified by flash column chromatography to provide methyl 2-(3,6-dichloro-2-hydroxy-phenyl)acetate (10.6 g, 99%) as a white solid.

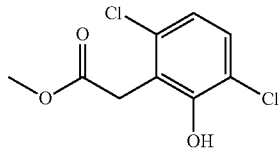

$^1$H NMR (400 MHz, CDCl$_3$): δ$_H$: 7.22 (d, 1H), 6.96 (d, 1H), 6.13 (br. s., 1H), 3.91 (s, 2H), 3.74 (s, 3H).

1.6 Methyl 2-[3,6-dichloro-2-[(4-methoxyphenyl)methoxy]phenyl]acetate 1-(Chloromethyl)-4-methoxy-benzene (13.6 mL, 101 mmol) was added to a suspension of methyl 2-(3,6-dichloro-2-hydroxy-phenyl)acetate (21.5 g, 91.5 mmol) and potassium carbonate (14.0 g, 101 mmol) in acetone (230 mL). The mixture was stirred at room temperature for 72 hours. The mixture was filtered and the filtrate was concentrated in vacuo. The crude product was purified by flash column chromatography to provide methyl 2-[3,6-dichloro-2-[(4-methoxyphenyl)methoxy]phenyl]acetate (22.5 g, 69%) as a yellow solid.

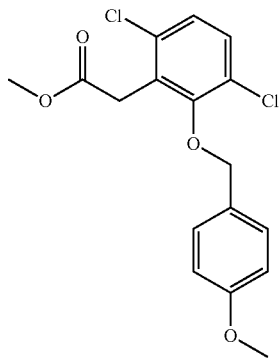

¹H NMR (400 MHz, CDCl₃): δ$_H$: 7.42-7.34 (m, 2H), 7.31 (d, 1H), 7.15 (d, 1H), 6.97-6.89 (m, 2H), 4.95 (s, 2H), 3.84 (s, 3H), 3.81 (s, 2H), 3.70 (s, 3H).

1.7 2-[3,6-Dichloro-2-[(4-methoxyphenyl)methoxy]phenyl]acetic acid

A solution of sodium hydroxide (12.7 g, 317 mmol) in water (127 mL) was added to a solution of methyl 2-[3,6-dichloro-2-[(4-methoxyphenyl)methoxy]phenyl]acetate (22.5 g, 63.3 mmol) in methanol (127 mL) and the mixture was heated at reflux for 3 hours. The mixture was allowed to cool to room temperature and was concentrated in vacuo. The residue was diluted with water (100 mL) and the mixture was acidified to pH 1 by the addition of hydrochloric acid (180 mL, 2.0 M) resulting in the formation of a precipitate. The mixture was filtered and the filtrand was dissolved in dichloromethane (150 mL). The mixture was dried over MgSO₄, passed through a hydrophobic frit and concentrated in vacuo. The crude product was recrystallized from dichloromethane-isohexane to provide 2-[3,6-dichloro-2-[(4-methoxyphenyl)methoxy]phenyl]acetic acid (15.0 g, 69%) as a beige solid.

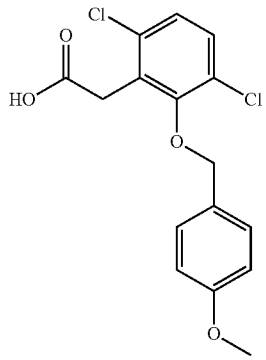 [SMILES: COc1ccc(COc2c(Cl)ccc(Cl)c2CC(=O)O)cc1]

¹H NMR (400 MHz, CDCl₃): δ$_H$: 7.40-7.34 (m, 2H), 7.32 (d, 1H), 7.15 (d, 1H), 6.95-6.86 (m, 2H), 4.96 (s, 2H), 3.83 (s, 2H), 3.82 (s, 3H).

1.8 Ethyl (2E/Z)-2-(methylhydrazono)propanoate

A solution of methylhydrazine (5.00 g, 109 mmol) in chloroform (20 mL) was added to a suspension of ethyl 2-oxopropanoate (12.9 g, 111 mmol) and MgSO₄ (13.3 g, 111 mmol) in chloroform (60 mL) at 0° C. The reaction mixture was allowed to warm to room temperature and was stirred for a further 16 hours. The reaction was filtered and the filtrate was concentrated in vacuo to provide ethyl-2-(methylhydrazono)propanoate (15.1 g, 96%) as a yellow oil, as a mixture of E/Z isomers.

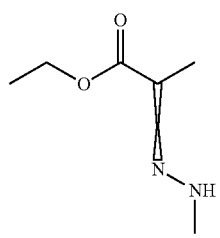

¹H NMR data for major isomer: (400 MHz, CDCl₃): δ$_H$: 5.58 (br. s, 1H), 4.30 (q, 2H), 3.24 (s, 3H), 1.92 (s, 3H), 1.34 (t, 3H).

1.9 Ethyl 2-[[2-[3,6-dichloro-2-[(4-methoxyphenyl)methoxy]phenyl]acetyl]-methyl-hydrazono]propanoate Oxalyl chloride (0.15 mL, 1.8 mmol) was added dropwise to a solution of 2-[3,6-dichloro-2-[(4-methoxyphenyl)methoxy]phenyl]acetic acid (0.50 g, 1.5 mmol) in a mixture of dichloromethane (7.3 mL) and N,N-dimethylformamide (0.1 mL). The mixture was stirred for 30 minutes until the effervescence ceased The mixture was concentrated in vacuo and the residue was dissolved in dichloromethane (5.0 mL) then added to a solution of ethyl (2E/Z)-2-(methylhydrazono)propanoate (0.21 g, 1.5 mmol) and pyridine (0.40 mL, 3.2 mmol) in dichloromethane (7.4 mL) at 0° C. The mixture was allowed to warm to room temperature then stirred for 16 hours. The mixture was washed with an aqueous solution of HCl (20 mL, 2.0 M) and a saturated aqueous solution of NaHCO₃ (20 mL). The organic extracts were dried over MgSO₄, passed through a hydrophobic frit and concentrated in vacuo. The crude product was purified by flash column chromatography to provide ethyl (2E/Z)-2-[[2-[3,6-dichloro-2-[(4-methoxyphenyl)methoxy]phenyl]acetyl]-methyl-hydrazono]propanoate (0.12 g, 17%) as an orange oil.

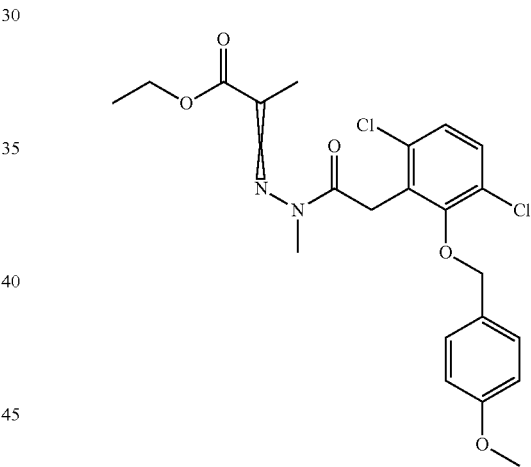

¹H NMR (400 MHz, CDCl₃): δ$_H$: 7.41-7.34 (m, 2H), 7.31-7.27 (m, 1H), 7.15 (d, 1H), 6.88 (d, 2H), 4.94 (s, 2H), 4.33 (q, 2H), 4.19 (s, 2H), 3.82 (s, 3H), 3.35 (s, 3H), 2.26 (s, 3H), 1.36 (t, 3H).

1.10 4-[3,6-Dichloro-2-[(4-methoxyphenyl)methoxy]phenyl]-2,6-dimethyl-pyridazine-3,5-dione 1,8-Diazabicyclo[5.4.0]undec-7-ene [DBU] (0.27 mL, 1.6 mmol) was added to a solution of ethyl (2E/Z)-2-[[2-[3,6-dichloro-2-[(4-methoxyphenyl)methoxy]phenyl]acetyl]-methyl-hydrazono]propanoate (0.30 g, 0.64 mmol) in acetonitrile (3.0 mL) in a microwave vial. The mixture was heated at 125° C. for 45 minutes then cooled to room temperature. The mixture was diluted with ethyl acetate (10 mL) then washed with hydrochloric acid (10 mL, 2.0 M). The combined organic extracts were dried over MgSO₄, passed through a hydrophobic frit and concentrated in vacuo. The crude product was purified by flash column chromatography to provide 4-[3,6-dichloro-2-[(4-methoxyphenyl)methoxy]phenyl]-5-hydroxy-2,6-dimethyl-pyridazin-3-one (0.14 g, 53%) as a white foam.

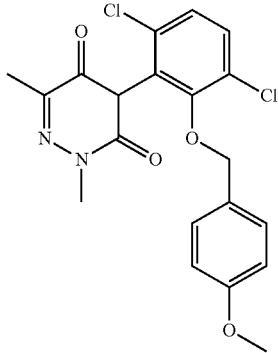

$^1$H NMR (400 MHz, CDCl$_3$): δ$_H$: 7.44 (d, 1H), 7.26 (d, 1H), 7.10-7.03 (m, 2H), 6.82-6.76 (m, 2H), 6.02 (br. s., 1H), 5.03 (d, 1H), 4.66 (d, 1H), 3.80 (s, 3H), 3.72 (s, 3H), 2.25 (s, 3H).

1.11 4-[3,6-Dichloro-2-[(4-methoxyphenyl)methoxy]phenyl]-5-(methoxymethoxy)-2,6-dimethyl-pyridazin-3-one Sodium hydride (0.076 g, 1.9 mmol) was added to a solution of 4-[3,6-dichloro-2-[(4-methoxyphenyl)methoxy]phenyl]-5-hydroxy-2,6-dimethyl-pyridazin-3-one (0.40 g, 0.95 mmol) in N,N-dimethylformamide (4.8 mL) at 0° C. and the mixture was stirred for 10 minutes. Chloromethyl methyl ether (0.15 g, 1.9 mmol) was added and the mixture was allowed to warm to room temperature. The mixture was stirred for 30 minutes then diluted with ethyl acetate (10 mL) and water (10 mL) then separated. The organic extracts were dried over MgSO$_4$, passed through a hydrophobic frit and concentrated in vacuo. The crude product was purified by flash column chromatography to provide 4-[3,6-dichloro-2-[(4-methoxyphenyl)methoxy]phenyl]-5-(methoxymethoxy)-2,6-dimethyl-pyridazin-3-one (0.37 g, 83%) as a colourless oil.

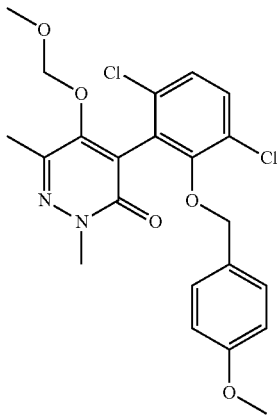

$^1$H NMR (400 MHz, CDCl$_3$): δ$_H$: 7.42 (d, 1H), 7.24 (d, 1H), 7.10 (d, 2H), 6.81 (d, 2H), 5.07 (d, 1H), 4.73-4.70 (m, 1H), 4.69-4.67 (m, 1H), 4.65 (d, 1H), 3.80 (s, 3H), 3.71 (s, 3H), 3.29 (s, 3H), 2.30 (s, 3H).

1.12 4-(3,6-Dichloro-2-hydroxy-phenyl)-5-(methoxymethoxy)-2,6-dimethyl-pyridazin-3-one 2,3-Dichloro-5,6-dicyano-p-benzoquinone [DDQ] (0.11 g, 0.50 mmol) was added to a solution of 4-[3,6-dichloro-2-[(4-methoxyphenyl)methoxy]phenyl]-5-(methoxymethoxy)-2,6-dimethyl-pyridazin-3-one (0.11 g, 0.24 mmol) in dichloromethane (1.2 mL). The mixture was stirred for 24 hours. The mixture was quenched by the addition of water (10 mL) then separated. The aqueous layer was extracted with dichloromethane (2×10 mL). The combined organic extracts were dried over MgSO$_4$, filtered and concentrated in vacuo. The crude product was purified by flash column chromatography to provide 4-(3,6-dichloro-2-hydroxy-phenyl)-5-(methoxymethoxy)-2,6-dimethyl-pyridazin-3-one (0.055 g, 67%) as a red solid.

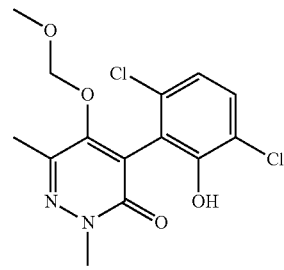 [SMILES: COCOc1c(C)nn(C)c(=O)c1-c1c(Cl)ccc(Cl)c1O]

$^1$H NMR (400 MHz, CDCl$_3$): δ$_H$: 7.35 (d, 1H), 7.03 (d, 1H), 4.72 (d, 1H), 4.62 (d, 1H), 3.81 (s, 3H), 3.34 (s, 3H), 2.40 (s, 3H).

1.13 4-[3,6-Dichloro-2-(2-pyridylmethoxy)phenyl]-2,6-dimethyl-pyridazine-3,5-dione trifluoroacetic acid salt (compound 1.01 as defined in Table 1)

Potassium carbonate (0.044 g, 0.32 mmol) was added to a solution of 4-(3,6-dichloro-2-hydroxy-phenyl)-5-(methoxymethoxy)-2,6-dimethyl-pyridazin-3-one (0.050 g, 0.14 mmol) and 2-(bromomethyl)pyridine hydrobromide (0.073 g, 0.29 mmol) in acetone (2.0 mL) and the mixture was heated at 60° C. for 4 hours. The mixture was allowed to cool to room temperature then filtered and the filtrate was concentrated in vacuo. The crude product was purified by flash column chromatography to provide an orange oil (0.012 g). The material was dissolved in methanol (0.14 mL) and an aqueous solution of HCl (2.0 M, 0.041 mL, 0.083 mmol) was added. The mixture was stirred overnight then concentrated in vacuo. The crude material was purified by preparative HPLC (eluting with 0.1% TFA in H$_2$O-MeCN) to provide 4-[3,6-dichloro-2-(2-pyridylmethoxy)phenyl]-5-hydroxy-2,6-dimethyl-pyridazin-3-one trifluoroacetate (0.0046 g, 6%) as a colourless oil.

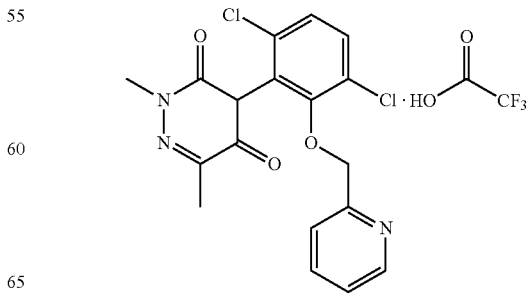

¹H NMR (400 MHz, methanol-d₄): $\delta_H$: 8.65 (dd, 1H), 8.33 (dt, 1H), 7.84-7.73 (m, 2H), 7.58 (d, 1H), 7.42 (d, 1H), 5.37-5.29 (m, 1H), 5.26-5.16 (m, 1H), 3.55 (s, 3H), 2.25 (s, 3H).

Example 2 Preparation of 4-[3,6-dichloro-2-[(2-chlorothiazol-5-yl)methoxy]phenyl]-2,6-dimethyl-pyridazine-3,5-dione

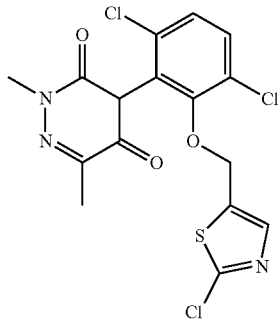 [SMILES: CC1=NN(C)C(=O)C(c2c(Cl)ccc(Cl)c2OCc2cnc(Cl)s2)C1=O]

2.1 2-Allyl-3,6-dichloro-phenol

A mixture of 2-allyloxy-1,4-dichloro-benzene (1.0 g, 4.9 mmol, 1.0 eq.) and N,N-dimethylformamide (0.1 mL) was heated at an external temperature of 220° C. for 1 hour. The mixture was allowed to cool to room temperature and was concentrated in vacuo to provide 2-allyl-3,6-dichloro-phenol as a brown oil (0.99 g, 99%).

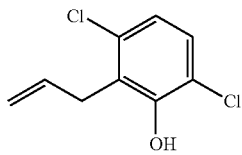

¹H NMR (400 MHz, CDCl₃): $\delta_H$: 7.18-7.08 (1H, m) 6.95-6.85 (1H, m) 6.02-5.84 (1H, m) 5.71 (1H, s) 5.14-4.99 (2H, m) 3.59 (2H, dt).

2.2 2-Allyl-1,4-dichloro-3-methoxy-benzene

Iodomethane (12.9 mL, 207 mmol) was added to a suspension of 2-allyl-3,6-dichloro-phenol (40.0 g, 197 mmol) and potassium carbonate (30.2 g, 217 mmol) in acetone (490 mL) and the mixture was stirred at 25° C. for 24 hours. The mixture was filtered and the filtrate was concentrated in vacuo. The residue was dissolved in a mixture of diethyl ether (150 mL) and water (150 mL) then separated. The organic extracts were dried over MgSO₄, passed through a hydrophobic frit and concentrated in vacuo to provide 2-allyl-1,4-dichloro-3-methoxy-benzene (38.0 g, 89%) as an orange oil.

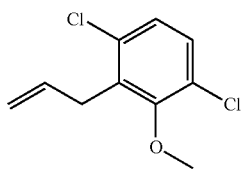

¹H NMR (400 MHz, CDCl₃): $\delta_H$: 7.23-7.17 (m, 1H), 7.14-7.07 (m, 1H), 6.03-5.90 (m, 1H), 5.12-4.96 (m, 2H), 3.86 (s, 3H), 3.58 (td, 2H).

2.3 2-(3,6-Dichloro-2-methoxy-phenyl)acetic acid

Ruthenium(III) chloride hydrate (0.355 g, 1.71 mmol) was added to a solution of 2-allyl-1,4-dichloro-3-methoxy-benzene (18.6 g, 85.7 mmol) in a mixture of water (250 mL), acetonitrile (170 mL) and ethyl acetate (170 mL). Sodium metaperiodate (91.8 g, 428 mmol) was added portion wise over a period of 30 minutes. The mixture was stirred for 10 minutes then cooled to 5° C. The mixture was quenched by the addition of an aqueous solution of sodium metabisulfite (65 wt %) over 2 hours. The mixture was diluted with brine (200 mL) then separated. The aqueous layer was extracted with ethyl acetate (3×200 mL). The combined organic extracts were dried over MgSO₄, filtered and concentrated in vacuo. The crude product was purified by flash column chromatography to provide 2-(3,6-dichloro-2-methoxy-phenyl)acetic acid (11.9 g, 59%) as a white solid.

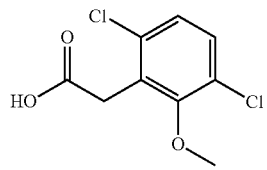

¹H NMR (400 MHz, CDCl₃): $\delta_H$: 7.28 (d, 1H), 7.14 (d, 1H), 3.93 (s, 2H), 3.88 (s, 3H).

2.4 2-(3,6-dichloro-2-methoxy-phenyl)-N-methyl-acetohydrazide

EDC hydrochloride [N-(3-dimethylaminopropyl)-N'-ethylcarbodiimide hydrochloride, CAS number: 25952-53-8] (0.98 g, 5.1 mmol) was added to a solution of 2-(3,6-dichloro-2-methoxy-phenyl)acetic acid (1.0 g, 4.3 mmol) in dichloromethane (21 mL). The mixture was stirred for 20 min and methylhydrazine (0.20 g, 0.22 mL, 4.3 mmol) was added. The reaction was stirred for 21 h.
The mixture was concentrated in vacuo and the crude product was purified by flash column chromatography. The desired hydrazide 2-(3,6-dichloro-2-methoxy-phenyl)-N-methyl-acetohydrazide (0.667 g, 60%) was obtained as a colourless oil which solidified on standing.

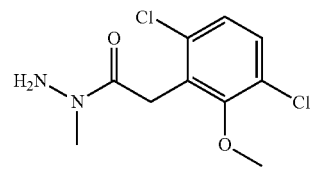 [SMILES: COc1c(Cl)ccc(Cl)c1CC(=O)N(C)N]

¹H NMR (400 MHz, CDCl₃): $\delta_H$ (ppm): 7.26-7.19 (m, 1H), 7.17-7.06 (m, 1H), 4.52 (br. s., 1H), 4.26-3.89 (m, 3H), 3.86 (s, 3H), 3.24 (s, 1H), 3.29-3.19 (m, 2H).

2.5 ethyl 2-[[2-(3,6-dichloro-2-methoxy-phenyl)acetyl]-methyl-hydrazono]propanoate Ethyl pyruvate (0.29 g, 0.28 mL, 2.5 mmol) was added to a solution of 2-(3,6-dichloro-2-methoxy-phenyl)-N-methylacetohydrazide (0.65 g, 2.5 mmol) in ethanol (12 mL) and the mixture heated at reflux for 2 h. The mixture was concentrated in vacuo to give ethyl 2-[[2-(3,6-dichloro-2-methoxy-phenyl)acetyl]-methyl-hydrazono]propanoate (0.866 g, 97%) as a colourless oil.

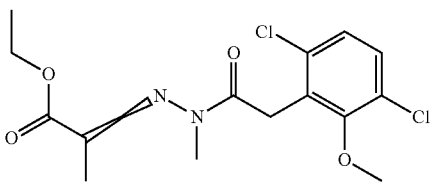

$^1$H NMR (400 MHz, CDCl$_3$): δ$_H$ (ppm): 7.27-7.21 (m, 1H), 7.12 (d, J=8.7, 1H), 4.33 (q, J=7.1, 2H), 4.20 (s, 2H), 3.84 (s, 3H), 3.42 (s, 3H), 2.33 (s, 3H), 1.37 (t, J=7.2, 3H).

2.6 4-(3,6-dichloro-2-methoxy-phenyl)-2,6-dimethyl-pyridazine-3,5-dione 1,8-Diazabicyclo[5.4.0]undec-7-ene [DBU] (0.90 g, 0.89 mL, 5.9 mmol) was added to a solution of ethyl 2-[[2-(3,6-dichloro-2-methoxy-phenyl)acetyl]-methyl-hydrazono]propanoate (0.85 g, 2.4 mmol) in acetonitrile (12 mL). The mixture was heated by microwave irradiation at 125° C. for 45 min then cooled to ambient temperature.

The mixture was diluted with ethyl acetate (30 mL) then washed with dilute hydrochloric acid (20 mL, 2.0 M). The organic extracts were dried over MgSO$_4$, filtered and concentrated in vacuo. The crude product was purified by flash column chromatography to provide 4-(3,6-dichloro-2-methoxy-phenyl)-2,6-dimethyl-pyridazine-3,5-dione (0.317 g, 43%) as a yellow solid.

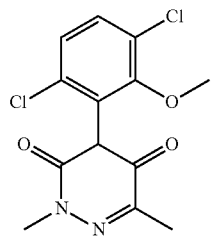

$^1$H NMR (400 MHz, DMSO-d$_6$): δ$_H$ (ppm): 10.70 (br. s., 1H), 7.56 (d, J=8.7, 1H), 7.36 (d, J=8.7, 1H), 3.60 (s, 3H), 3.58 (s, 3H), 2.24 (s, 3H).

2.7 4-(3,6-dichloro-2-hydroxy-phenyl)-2,6-dimethyl-pyridazine-3,5-dione

Hydrobromic acid (48% aqueous solution) (0.94 g, 0.63 mL, 5.6 mmol) was added to 4-(3,6-dichloro-2-methoxy-phenyl)-2,6-dimethyl-pyridazine-3,5-dione (0.10 g, 0.32 mmol) and the mixture heated at reflux for 4 h. The mixture was allowed to cool to ambient temperature then extracted with ethyl acetate (3×10 mL). The combined organic extracts were dried over MgSO$_4$, filtered and concentrated in vacuo to provide 4-(3,6-dichloro-2-hydroxy-phenyl)-2,6-dimethyl-pyridazine-3,5-dione (64 mg, 67%) as an orange foam.

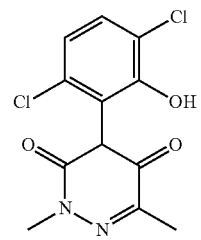 [SMILES: CC1=NN(C)C(=O)C(c2c(Cl)ccc(Cl)c2O)C1=O]

$^1$H NMR (400 MHz, DMSO-d$_6$): δ$_H$ (ppm): 10.49 (br. s., 1H), 9.52 (br. s., 1H), 7.40 (d, J=8.7, 1H), 7.00 (d, J=8.6, 1H), 3.56 (s, 3H), 2.21 (s, 3H).

2.8 4-[3,6-dichloro-2-[(2-chlorothiazol-5-yl) methoxy]phenyl]-2,6-dimethyl-pyridazine-3,5-dione (compound 1.19 as defined in Table 1)

Sodium hydride (60% in mineral oil) (0.11 g, 2.8 mmol) was suspended in N,N-dimethylformamide (6.6 mL) under N$_2$ atmosphere. A solution of 4-(3,6-dichloro-2-hydroxy-phenyl)-2,6-dimethyl-pyridazine-3,5-dione (0.40 g, 1.3 mmol) in N,N-dimethylformamide (6.6 mL) was added at ambient temperature. The mixture was stirred for 5 min, resulting in a yellow solution. A solution of 2-chloro-5-(chloromethyl)thiazole (0.25 g, 1.5 mmol) in N,N-dimethylformamide (1.0 mL) was added and the mixture stirred for 3 h, resulting in the formation of a precipitate. The mixture was poured into a mixture of water (10 mL) and ice (10 g) then acidified to pH 1 by addition of dilute hydrochloric acid (10 mL, 2.0 M). The mixture was extracted with ethyl acetate (3×10 mL), the combined organic extracts dried over MgSO$_4$, passed through a hydrophobic frit and concentrated in vacuo. The crude product was partially purified by flash column chromatography to provide a white foam. Further purification by preparative HPLC gave product 4-[3,6-dichloro-2-[(2-chlorothiazol-5-yl)methoxy]phenyl]-5-hydroxy-2,6-dimethyl-pyridazin-3-one (242 mg, 42%) as a white solid.

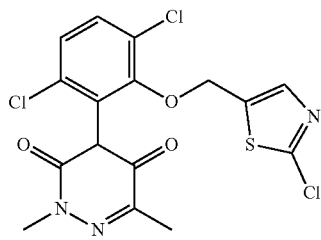 [SMILES: CC1=NN(C)C(=O)C(c2c(Cl)ccc(Cl)c2OCc2cnc(Cl)s2)C1=O]

$^1$H NMR (400 MHz, DMSO-d$_6$): δ$_H$ (ppm): 10.76 (s, 1H), 7.61 (d, J=8.7, 1H), 7.55 (s, 1H), 7.42 (d, J=8.7, 1H), 5.15-5.10 (m, 1H), 5.05-4.96 (m, 1H), 3.56 (s, 3H), 2.22 (s, 3H).

Compounds 1.01, 1.02, 1.03, 1.04, 1.06, 1.12, 1.13, 1.14, 1.19, 1.20, 1.21, 1.23, 1.24, 1.25, 1.27, 1.33, 1.34, 1.35, 1.40, 4.19, 4.40, 5.01 and 5.02 were prepared using the general methods as described supra. Table 6 below shows the structure of these compounds and NMR characterising data.

TABLE 6

Physical data for compounds of formula (I), wherein T is Tp, $X^{23}$ is H, $X^{24}$ is Cl, and G is H, and $R^1$, $R^2$, $X^{21}$, $X^{22}$ and D are as shown in the table. A hyphen or ~ indicates the point of attachment to the rest of the molecule.

| Compound | $R^1$ | $R^2$ | $X^{21}$ | $X^{22}$ | D | NMR details |
|---|---|---|---|---|---|---|
| 1.01 | Me | Me | Cl | H | 2-pyridyl- | (as trifluoroacetate salt) $^1$H NMR (400 MHz, d4-methanol) $\delta_H$: 8.65 (dd, 1H), 8.33 (dt, 1H), 7.84-7.73 (m, 2H), 7.58 (d, 1H), 7.42 (d, 1H), 5.37-5.29 (m, 1H), 5.26-5.16 (m, 1H), 3.55 (s, 3H), 2.25 (s, 3H). |
| 1.02 | Me | Me | Cl | H | 3-pyridyl- | $^1$H NMR (400 MHz, d6-DMSO) $\delta_H$: 10.87 (bs, 1H), 8.67 (s, 1H), 8.52 (s, 1H), 7.91 (d, J = 7.84, 1H), 7.67-7.61 (m, 2H), 7.42 (d, J = 8.72, 1H), 5.04 (d, J = 12.3, 1H), 4.94 (d, J = 12.3, 1H), 3.48 (s, 3H), 2.15 (s, 3H). |
| 1.03 | Me | Me | Cl | H | 4-pyridyl- | $^1$H NMR (400 MHz, d6-DMSO) $\delta_H$: 10.89 (bs, 1H), 8.69 (s, 2H), 7.64 (d, J = 8.72, 1H), 7.45-7.43 (m, 3H), 5.11 (d, J = 14.4, 1H), 4.97 (d, J = 14.64, 1H), 3.41 (s, 3H), 2.13 (s, 3H). |
| 1.04 | Me | Me | Cl | H | 2-thiazolyl- | $^1$H NMR (400 MHz, d6-DMSO) $\delta_H$: 10.82 (bs, 1H), 7.76 (s, 2H), 7.64 (d, J = 8.7, 1H), 7.45 (d, J = 8.7, 1H), 5.20 (d, J = 12.2, 1H), 5.10 (d, J = 12.2, 1H), 3.53 (s, 3H), 2.20 (s, 3H). |
| 1.06 | Me | Me | Cl | H | 5-thiazolyl- | $^1$H NMR (400 MHz, d6-DMSO) $\delta_H$: 10.77 (bs, 1H), 9.08 (s, 1H), 7.79 (s, 1H), 7.60 (d, J = 8.7, 1H), 7.41 (d, J = 8.7, 1H), 5.17 (d, J = 11.6, 1H), 5.04 (d, J = 11.6, 1H), 3.57 (s, 3H), 2.21 (s, 3H). |
| 1.12 | Me | Me | Cl | H | 2-methylthiazol-4-yl-methyl | $^1$H NMR (400 MHz, d6-DMSO) $\delta_H$: 10.63 (bs, 1H), 7.58 (d, J = 8.7, 1H), 7.38 (d, J = 8.7, 1H), 7.18 (s, 1H), 4.89 (d, J = 11.6, 1H), 4.80 (d, J = 11.5, 1H), 3.53 (s, 3H), 2.57 (s, 3H), 2.18 (s, 3H). |
| 1.13 | Me | Me | Cl | H | 4-methylthiazol-2-yl-methyl | $^1$H NMR (400 MHz, d6-DMSO) $\delta_H$: 10.79 (bs, 1H), 7.63 (d, J = 8.7, 1H), 7.44 (d, J = 8.7, 1H), 7.26 (s, 1H), 5.13 (d, J = 12.2, 1H), 5.03 (d, J = 12.3, 1H), 3.53 (s, 3H), 2.34 (s, 3H), 2.19 (s, 3H). |
| 1.14 | Me | Me | Cl | H | 2-chloropyridin-4-yl-methyl | $^1$H NMR (400 MHz, d6-DMSO) $\delta_H$: 10.85 (bs, 1H), 8.32 (d, J = 5.0, 1H), 7.61 (d, J = 8.7, 1H), 7.41 (d, J = 8.7, 1H), 7.17 (d, J = 4.4, 2H), 5.02 (d, J = 14.2, 1H), 4.88 (d, J = 14.1, 1H), 3.41 (s, 3H), 2.11 (s, 3H). |

TABLE 6-continued

Physical data for compounds of formula (I), wherein T is Tp, $X^{23}$ is H, $X^{24}$ is Cl, and G is H, and $R^1$, $R^2$, $X^{21}$, $X^{22}$ and D are as shown in the table. A hyphen or ~ indicates the point of attachment to the rest of the molecule.

| Compound | $R^1$ | $R^2$ | $X^{21}$ | $X^{22}$ | D | NMR details |
|---|---|---|---|---|---|---|
| 1.19 | Me | Me | Cl | H | 2-chloro-thiazol-4-yl (attached via CH2) | $^1$H NMR (400 MHz, d6-DMSO) $\delta_H$: 10.75 (s, 1H), 7.61 (d, J = 8.64, 1H), 7.55 (s, 1H), 7.42 (d, J = 8.72, 1H), 5.13 (d, J = 12.3, 1H), 5.01 (d, J = 12.3, 1H), 3.56 (s, 3H), 2.22 (s, 3H). |
| 1.20 | Me | Me | Cl | H | 5-chloro-thiophen-2-yl | $^1$H NMR (400 MHz, CDCl$_3$) $\delta_H$: 10.75 (s, 1H), 7.60 (d, J = 8.8, 1H), 7.41 (d, J = 8.8, 1H), 6.97 (d, J = 3.8, 1H), 6.87 (d, J = 3.8, 1H), 5.08-4.97 (m, 1H), 4.92-4.82 (m, 1H), 3.57 (s, 3H), 2.23 (s, 3H). |
| 1.21 | Me | Me | Cl | H | 5-methyl-pyrazin-2-yl | $^1$H NMR (400 MHz, d6-DMSO) $\delta_H$: 10.75 (br. s., 1H), 8.42 (d, J = 0.9, 1H), 8.29 (d, J = 1.2, 1H), 7.61 (d, J = 8.7, 1H), 7.41 (d, J = 8.8, 1H), 5.05-4.95 (m, 1H), 4.94-4.84 (m, 1H), 3.47 (s, 3H), 2.48 (s, 3H), 2.13 (s, 3H). |
| 1.23 | Me | Me | F | H | 3-pyridyl- | $^1$H NMR (400 MHz, d6-DMSO) $\delta_H$: 10.88 (bs, 1H), 8.65 (d, J = 3.9, 1H), 8.52 (s, 1H), 7.89 (d, J = 7.6, 1H), 7.65-7.59 (m, 2H), 7.18 (t, J = 8.7, 1H), 5.06 (d, J = 12.2, 1H), 4.93 (d, J = 12.2, 1H), 3.48 (s, 3H), 2.16 (s, 3H). |
| 1.24 | Me | Me | F | H | 4-pyridyl- | $^1$H NMR (400 MHz, d6-DMSO) $\delta_H$: 10.84 (bs, 1H), 8.74 (bs, 2H), 7.68-7.64 (m, 1H), 7.59 (m, 2H), 7.21 (t, J = 8.7, 1H), 5.19 (d, J = 14.8, 1H), 5.03 (d, J = 14.8, 1H), 3.42 (s, 3H), 2.14 (s, 3H). |
| 1.25 | Me | Me | F | H | 2-thiazolyl- | $^1$H NMR (400 MHz, d6-DMSO) $\delta_H$: 10.88 (bs, 1H), 7.75 (s, 2H), 7.67-7.63 (m, 1H), 7.21 (t, J = 8.7, 1H), 5.24 (d, J = 12.2, 1H), 5.12 (d, J = 12.2, 1H), 3.53 (s, 3H), 2.20 (s, 3H). |
| 1.27 | Me | Me | F | H | 5-thiazolyl- | $^1$H NMR (400 MHz, d6-DMSO) $\delta_H$: 10.84 (bs, 1H), 9.08 (s, 1H), 7.79 (s, 1H), 7.61-7.58 (m, 1H), 7.18-7.14 (m, 1H), 5.21 (d, J = 11.6, 1H), 3.55 (s, 3H), 2.19 (s, 3H). |
| 1.33 | Me | Me | F | H | 2-methyl-thiazol-4-yl | $^1$H NMR (400 MHz, d6-DMSO) $\delta_H$: 10.67 (bs, 1H), 7.62-7.58 (m, 1H), 7.21 (s, 1H), 7.15 (t, J = 8.7, 1H), 4.92 (d, J = 11.6, 1H), 4.79 (d, J = 11.6, 1H), 3.53 (s, 3H), 2.57 (s, 3H), 2.19 (s, 3H). |

TABLE 6-continued

Physical data for compounds of formula (I), wherein T is Tp, $X^{23}$ is H, $X^{24}$ is Cl, and G is H, and $R^1$, $R^2$, $X^{21}$, $X^{22}$ and D are as shown in the table. A hyphen or ~ indicates the point of attachment to the rest of the molecule.

| Compound | $R^1$ | $R^2$ | $X^{21}$ | $X^{22}$ | D | NMR details |
|---|---|---|---|---|---|---|
| 1.34 | Me | Me | F | H | 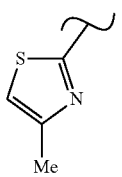 | $^1$H NMR (400 MHz, d6-DMSO) $\delta_H$: 10.84 (bs, 1H), 7.66-7.62 (m, 1H), 7.26 (s, 1H), 7.20 (t, J = 8.7, 1H), 5.17 (d, J = 12.2, 1H), 5.04 (d, J = 12.2, 1H), 3.53 (s, 3H), 2.31 (s, 3H), 2.19 (s, 3H). |
| 1.35 | Me | Me | F | H | 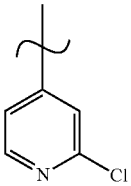 | $^1$H NMR (400 MHz, d6-DMSO) $\delta_H$: 10.89 (bs, 1H), 8.32 (d, J = 5, 1H), 7.66-7.62 (m, 1H), 7.21-7.17 (m, 3H), 5.04 (d, J = 14, 1H), 4.87 (d, J = 14, 1H), 3.44 (s, 3H), 2.14 (s, 3H). |
| 1.40 | Me | Me | F | H | 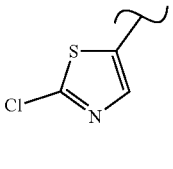 | $^1$H NMR (400 MHz, d6-DMSO) $\delta_H$: 10.81 (bs, 1H), 7.64-7.60 (m, 1H), 7.53 (s, 1H), 7.17 (t, J = 8.7, 1H), 5.16 (d, J = 12.4, 1H), 5.03 (d, J = 12.4, 1H), 3.55 (s, 3H), 2.21 (s, 3H). |
| 4.19 | —CH$_2$C≡CH | Me | Cl | H | 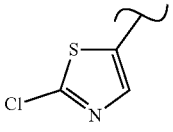 | $^1$H NMR (400 MHz, CDCl$_3$) $\delta_H$: 7.35 (d, 1H), 7.30 (s, 1H), 7.20 (d, 1H), 5.18-5.10 (m, 1H), 5.01-4.87 (m, 2H), 4.73 (dd, 1H), 2.36-2.30 (m, 4H). |
| 4.40 | —CH$_2$C≡CH | Me | F | H | 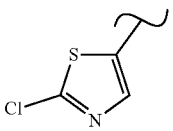 | $^1$H NMR (400 MHz, CDCl$_3$) $\delta_H$: 7.50 (dd, J = 9.0 and 5.6, 1H), 7.36 (s, 1H), 7.02 (t, J = 8.6, 1H), 5.27 (d, J = 12.2, 1H), 5.02-4.82 (m, 3H), 2.37-2.32 (m, 4H). |
| 5.01 | Me | Me | Cl | Cl | 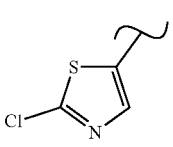 | $^1$H NMR (400 MHz, CDCl$_3$) $\delta_H$: 10.92 (br. s., 1H), 8.04 (s, 1H), 7.54 (br. s., 1H), 5.17-5.08 (m, 1H), 5.06-4.96 (m, 1H), 3.55 (br. s., 3H), 2.21 (br. s., 3H). |
| 5.02 | Me | Cl | Cl | H | 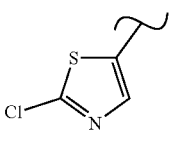 | $^1$H NMR (400 MHz, CDCl$_3$) $\delta_H$: 7.34 (d, J = 8.7, 1H), 7.28 (s, 1H), 7.18 (d, J = 8.7, 1H), 5.19 (dd, J = 12.3 and 0.6, 1H), 4.93 (d, J = 12.8, 1H), 3.71 (s, 3H). |

BIOLOGICAL EXAMPLES

B1 Post-Emergence Efficacy

Seeds of a variety of test species are shown in standard soil in pots:—*Solanum nigrum* (SOLNI), *Amaranthus retroflexus* (AMARE), *Setaria faberi* (SETFA), *Echinochloa crus-galli* (ECHCG), *Ipomoea hederacea* (IPOHE), *Lolium perenne* (LOLPE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethylene sorbitan monolaurate, CAS RN 9005-64-5). Compounds are applied at 1000 and 62.5 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are assessed on a five point scale (5=80-100%; 4=60-79%; 3=40-59%; 2=20-39%; 1=0-19%).

TABLE 7

Control of weed species by compounds of formula
(I) after post-emergence application

| Compound | Application rate (g/ha) | AMARE | SOLNI | SETFA | LOLPE | ECHCG | IPOHE |
|---|---|---|---|---|---|---|---|
| 1.02 | 1000 | 4 | 5 | 5 | 4 | 4 | 5 |
|  | 62.5 | 4 | 4 | 3 | 2 | 3 | 3 |
| 1.03 | 1000 | 4 | 5 | 5 | 4 | 5 | 4 |
|  | 62.5 | 1 | 4 | 1 | 1 | 2 | 4 |
| 1.04 | 1000 | 5 | 5 | 5 | 5 | 5 | 5 |
|  | 62.5 | 5 | 5 | 5 | 3 | 4 | 5 |
| 1.06 | 1000 | 5 | 5 | 5 | 5 | 5 | 5 |
|  | 62.5 | 4 | 5 | 5 | 4 | 5 | 5 |
| 1.12 | 1000 | 5 | 5 | 5 | 4 | 4 | 5 |
|  | 62.5 | 3 | 3 | 2 | 1 | 2 | 4 |
| 1.13 | 1000 | 4 | 5 | 5 | 4 | 5 | 5 |
|  | 62.5 | 3 | 4 | 4 | 2 | 3 | 4 |
| 1.14 | 1000 | 5 | 5 | 5 | 5 | 5 | 5 |
|  | 62.5 | 5 | 4 | 4 | 3 | 4 | 5 |
| 1.19 | 1000 | 5 | 5 | 5 | 5 | 5 | 5 |
|  | 62.5 | 5 | 5 | 5 | 5 | 3 | 5 |
| 1.20 | 1000 | 3 | 5 | 5 | 4 | 5 | 5 |
|  | 62.5 | 1 | 5 | 2 | 2 | 2 | 5 |
| 1.21 | 1000 | 3 | 4 | 5 | 2 | 4 | 5 |
|  | 62.5 | 2 | 3 | 3 | 1 | 1 | 4 |
| 1.23 | 1000 | 5 | 5 | 5 | 5 | 5 | 5 |
|  | 62.5 | 4 | 4 | 2 | 2 | 2 | 4 |
| 1.24 | 1000 | 5 | 5 | 5 | 5 | 5 | 5 |
|  | 62.5 | 2 | 4 | 1 | 1 | 3 | 4 |
| 1.25 | 1000 | 5 | 5 | 5 | 5 | 5 | 5 |
|  | 62.5 | 5 | 5 | 5 | 4 | 4 | 5 |
| 1.33 | 1000 | 5 | 5 | 5 | 4 | 4 | 5 |
|  | 62.5 | 3 | 4 | 2 | 2 | 3 | 4 |
| 1.34 | 1000 | 5 | 5 | 5 | 4 | 5 | 5 |
|  | 62.5 | 4 | 5 | 4 | 3 | 4 | 5 |
| 1.40 | 1000 | 5 | 5 | 5 | 5 | 5 | 5 |
|  | 62.5 | 5 | 5 | 5 | 5 | 5 | 5 |
| 4.19 | 1000 | 5 | 5 | 5 | 5 | 5 | 5 |
|  | 62.5 | 5 | 5 | 5 | 5 | 5 | 5 |
| 4.40 | 1000 | 5 | 5 | 5 | 5 | 5 | 5 |
|  | 62.5 | 4 | 5 | 5 | 5 | 5 | 5 |
| 5.01 | 1000 | 5 | 5 | 5 | 5 | 5 | 5 |
|  | 62.5 | 3 | 5 | 2 | 2 | 2 | 5 |

The invention claimed is:

1. A compound of formula (I)

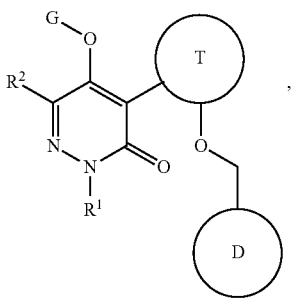

or a salt or N-oxide thereof, $R^1$ is selected from the group consisting of $C_1$-$C_4$-alkyl, $C_3$-$C_6$-cycloalkyl, $C_1$-$C_2$-alkoxy-$C_1$-$C_2$-alkyl, $C_2$-$C_4$-alkenyl, $C_1$-$C_4$-haloalkyl, $C_2$-$C_4$-haloalkenyl, $C_2$-$C_4$-alkynyl and $C_2$-$C_4$-haloalkynyl;

$R^2$ is selected from the group consisting of hydrogen, halogen, cyano, $C_1$-$C_6$-alkyl, $C_1$-$C_6$-haloalkyl, $C_1$-$C_6$-haloalkoxy, $C_1$-$C_3$-haloalkoxy-$C_1$-$C_3$-alkyl-, $C_1$-$C_6$-alkoxy, $C_1$-$C_3$-alkoxy-$C_1$-$C_3$-alkyl, $C_1$-$C_3$-alkoxy-$C_1$-$C_3$-alkoxy-$C_1$-$C_3$-alkyl-, $C_3$-$C_6$-cycloalkyl, $C_2$-$C_6$-alkenyl, $C_2$-$C_6$-haloalkenyl, $C_2$-$C_6$-alkynyl, $C_1$-$C_6$-hydroxyalkyl-, $C_1$-$C_6$-alkylcarbonyl-, $C_1$-$C_6$-alkyl-S(O)$_m$—, amino, $C_1$-$C_6$-alkylamino, $C_1$-$C_6$-dialkylamino, —C($C_1$-$C_3$-alkyl)=N—O—$C_1$-$C_3$-alkyl and $C_2$-$C_6$-haloalkynyl;

G is hydrogen, or C(O)$R^3$;

$R^3$ is selected from the group consisting of $C_1$-$C_6$-alkyl, $C_1$-$C_6$-alkenyl, $C_1$-$C_6$-alkynyl, $C_1$-$C_6$-alkoxy, $C_1$-$C_6$-alkyl-S—, —NR$^4$R$^5$ and phenyl, wherein said phenyl is optionally substituted by one or more $R^6$;

$R^4$ and $R^5$ are independently selected from the group consisting of $C_1$-$C_6$-alkyl and $C_1$-$C_6$-alkoxy, or $R^4$ and $R^5$ together can form a morpholinyl ring;

$R^6$ is selected from the group consisting of halogen, cyano, nitro, $C_1$-$C_3$-alkyl, $C_1$-$C_3$-haloalkyl, $C_1$-$C_3$-alkoxy and $C_1$-$C_3$-haloalkoxy; and T is a 5- or 6-membered monocyclic heteroaryl ring system containing 1, 2, or 3 heteroatoms independently selected from nitrogen, oxygen and sulphur, said 5-membered ring system being substituted by one or more radicals selected from X, Y, and $R^7$, and said 6-membered ring system being substituted by one or more radicals selected from $X^1$, $X^2$, $X^3$, $X^4$ and $R^7$, and wherein the oxy-alkyl-D moiety and the pyridazine dione or pyridazinone moiety are linked via ring T such that they are situated ortho with respect to each other;

or T is a substituted phenyl ring of formula (Tp)

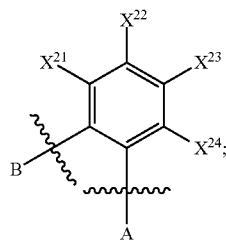

each X, $X^3$, $X^{23}$ and each Y are independently hydrogen, $C_1$-$C_3$-alkyl, $C_1$-$C_3$-alkoxy, $C_1$-$C_3$-haloalkyl, $C_1$-$C_3$-haloalkoxy, or halogen;

$X^1$ is oxo, $C_1$-$C_3$-alkyl, $C_1$-$C_3$-alkoxy, $C_1$-$C_3$-haloalkyl, $C_1$-$C_3$-haloalkoxy, or halogen;

$X^2$, and $X^4$ are independently hydrogen, $C_1$-$C_3$-alkyl, $C_1$-$C_3$-alkoxy, $C_1$-$C_3$-haloalkyl, $C_1$-$C_3$-haloalkoxy, oxo, or halogen;

$X^{21}$ is $C_1$-$C_3$-alkyl, $C_1$-$C_3$-alkoxy, $C_1$-$C_3$-haloalkyl, $C_1$-$C_3$-haloalkoxy, or halogen;

$X^{22}$, and $X^{24}$ are independently hydrogen, $C_1$-$C_3$-alkyl, $C_1$-$C_3$-alkoxy, $C_1$-$C_3$-haloalkyl, $C_1$-$C_3$-haloalkoxy, or halogen;

$R^7$ is hydrogen, $C_1$-$C_3$-alkyl, $C_1$-$C_3$-alkoxy, $C_1$-$C_3$-haloalkyl, or $C_1$-$C_3$-haloalkoxy;

A denotes the point of attachment to the oxy-alkyl-D moiety and B denotes the point of attachment to the pyridazine dione or pyridazinone moiety; and D is a substituted or unsubstituted 5- or 6-membered monocyclic heteroaryl ring containing 1, 2, or 3 heteroatoms independently selected from oxygen, nitrogen and sulphur, and wherein when D is substituted it is substituted on at least one ring carbon atom with $R^8$ and/or on a ring nitrogen atom with $R^9$;

each $R^8$ is independently oxygen, hydroxyl, halogen, cyano, $C_1$-$C_6$-alkyl, $C_1$-$C_6$-haloalkyl, $C_1$-$C_6$-haloalkoxy, $C_1$-$C_3$-haloalkoxy-$C_1$-$C_3$-alkyl-, $C_1$-$C_6$-alkoxy, $C_1$-$C_3$-alkoxy-$C_1$-$C_3$-alkyl, $C_1$-$C_3$-alkoxy-$C_1$-$C_3$-alkoxy-$C_1$-$C_3$-alkyl-, $C_3$-$C_6$-cycloalkyl, $C_2$-$C_6$-alkenyl, $C_2$-$C_6$-haloalkenyl, $C_2$-$C_6$-alkynyl, $C_1$-$C_6$-hydroxyalkyl-, $C_1$-$C_6$-alkylcarbonyl-, $C_1$-$C_6$-alkyl-S(O)m—, amino, $C_1$-$C_6$-alkylamino, $C_1$-$C_6$-dialkylamino, —C($C_1$-$C_3$alkyl)=N—O—$C_1$-$C_3$-alkyl or $C_2$-$C_6$-haloalkynyl;

each $R^9$ is independently, $C_1$-$C_4$-alkyl, $C_3$-$C_6$-alkoxy, $C_1$-$C_2$-alkoxy-$C_1$-$C_2$-alkyl, $C_2$-$C_4$-alkenyl, $C_1$-$C_4$-haloalkyl, $C_2$-$C_4$-haloalkenyl, $C_2$-$C_4$-alkynyl or $C_2$-$C_4$-haloalkynyl; and m is an integer of 0, 1, or 2.

2. The compound according to claim 1, wherein G is hydrogen, or C(O)$R^3$ wherein $R^3$ is $C_1$-$C_4$-alkyl, $C_1$-$C_4$-alkoxy, $C_2$-$C_3$-alkenyl, or C2-C3-alkynyl.

3. The compound according to claim 1, wherein D is a substituted or unsubstituted furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyridonyl, pyrimidinyl, pyridazinyl, pyrazinyl, 1,2,3-triazinyl, 1,2,4-triazinyl, or 1,3,5-triazinyl ring, wherein when D is substituted it is substituted on at least one ring carbon atom with $R^8$ and/or on a ring nitrogen atom with $R^9$.

4. The compound according to claim 1, wherein T is selected from any one of (Tp) or (T1) to (T62):

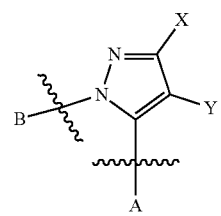

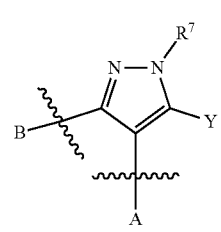

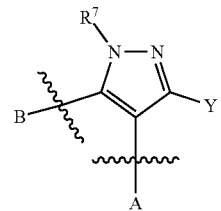

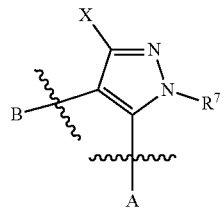

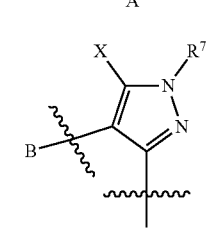

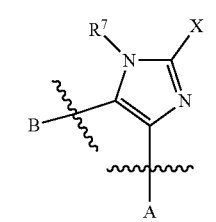

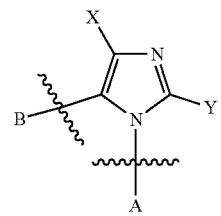

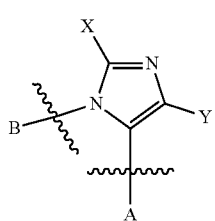 (T8)
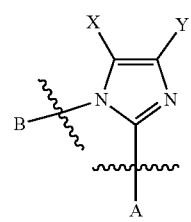 (T9)
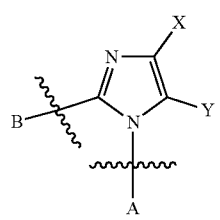 (T10)
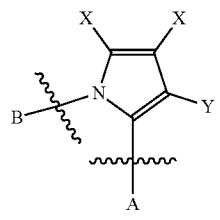 (T11)
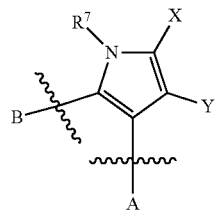 (T12)
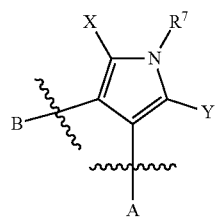 (T13)
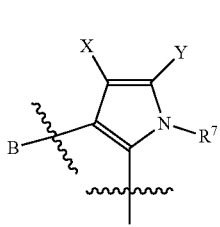 (T14)
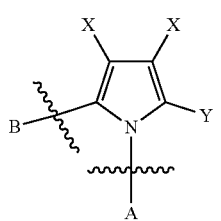 (T15)
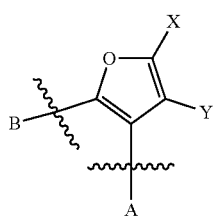 (T16)
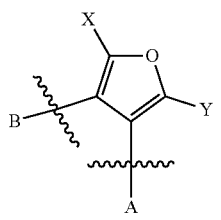 (T17)
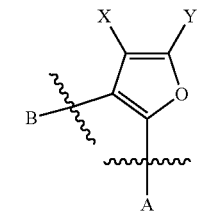 (T18)
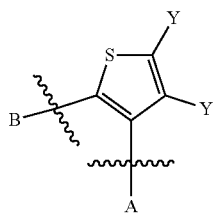 (T19)
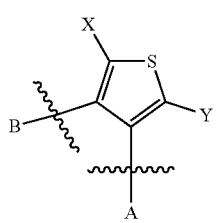 (T20)
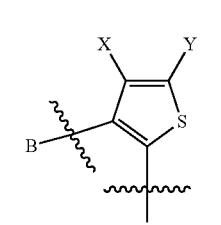 (T21)

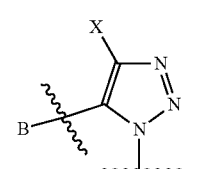 (T22)
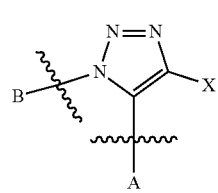 (T23)
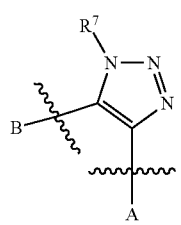 (T24)
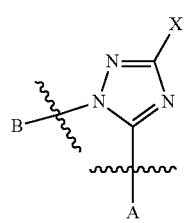 (T25)
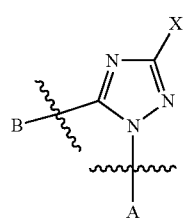 (T26)
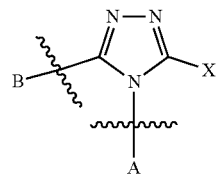 (T27)
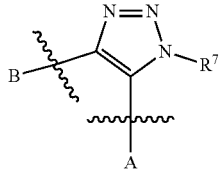 (T28)
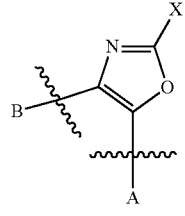 (T29)
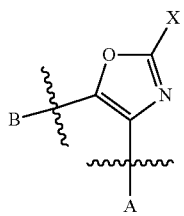 (T30)
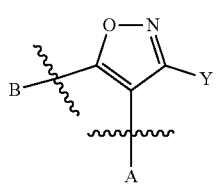 (T31)
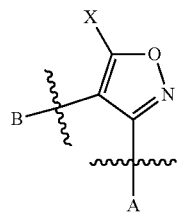 (T32)
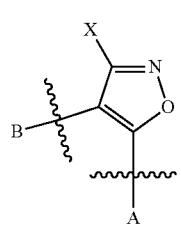 (T33)
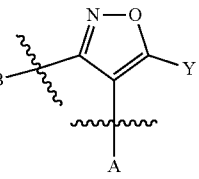 (T34)
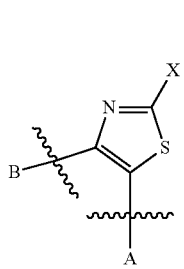 (T35)
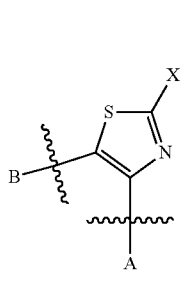 (T36)

(T37)
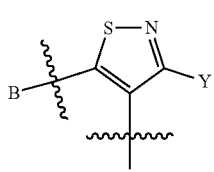
(T38)
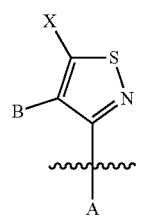
(T39)
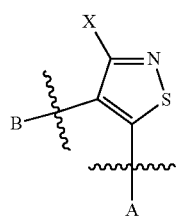
(T40)
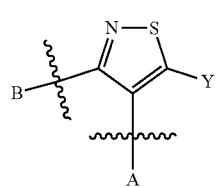
(T41)
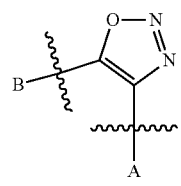
(T42)
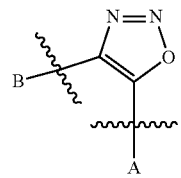
(T43)
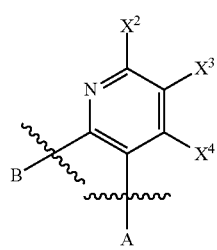
(T44)
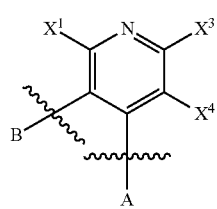
(T45)
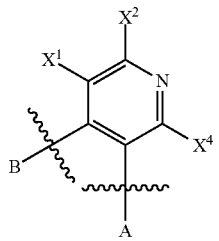
(T46)
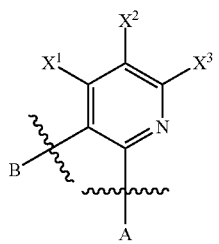
(T47)
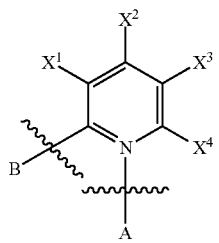
(T48)
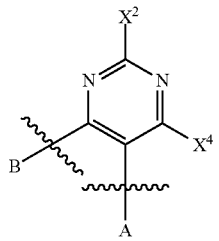
(T49)
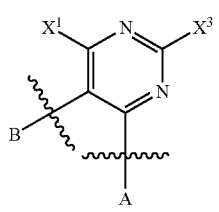
(T50)
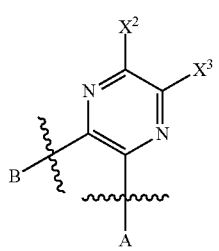

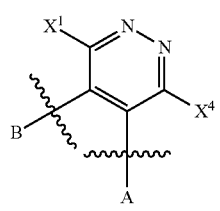 (T51)
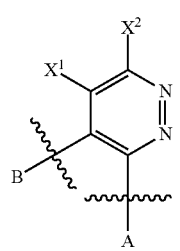 (T52)
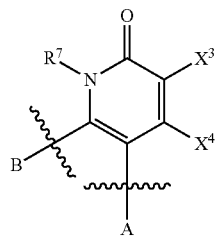 (T53)
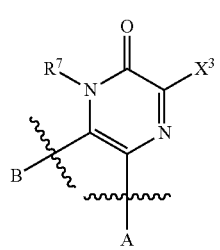 (T54)
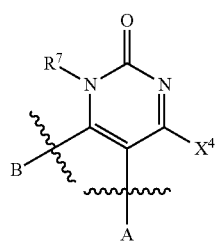 (T55)
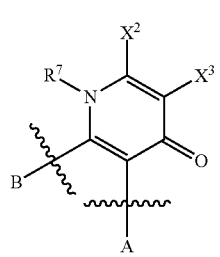 (T56)
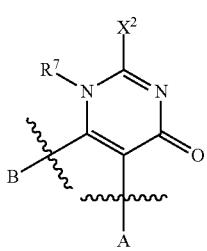 (T57)
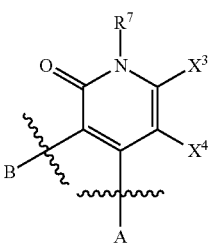 (T58)
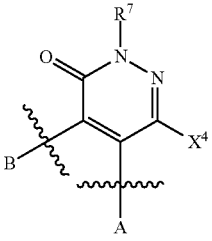 (T59)
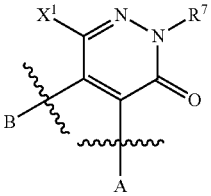 (T60)
(T61)
(T62)
wherein X, $X^1$, $X^2$, $X^3$, $X^4$, Y, $R^7$, A and B are as defined in claim 1.

5. The compound according to claim 1, wherein T is (Tp) or T is selected from the group consisting of (T1), (T2), (T3), (T4) and (T5):

(T1) 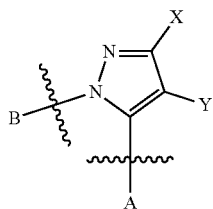

(T2) 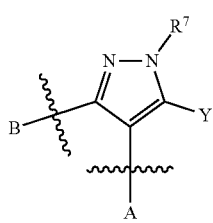

(T3) 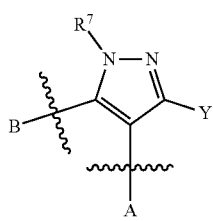

(T4) 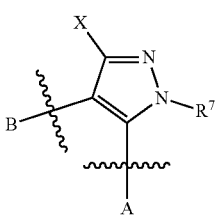

(T5) 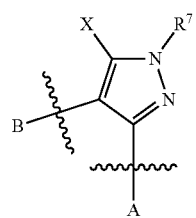

wherein,

X, Y, , A and B are as defined in claim 1,

A denotes the point of attachment to the oxy-alkyl-D moiety and B denotes the point of attachment to the pyridazine dione or pyridazinone moiety.

6. The compound according to claim 5, wherein T is selected from the group consisting of (T1), (T4), and (T5), and X is hydrogen or halogen.

7. The compound according to claim 5, wherein T is selected from the group consisting of (T1), (T2), and (T3), and Y is hydrogen, $C_1$-$C_3$-alkyl, $C_1$-$C_3$-haloalkyl, or halogen.

8. The compound according to claim 5, wherein T is selected from the group consisting of (T2), (T3), (T4), and (T5) wherein $R^7$ is $C_1$-$C_3$-alkyl, or $C_1$-$C_3$-haloalkyl.

9. The compound according to claim 1, wherein T is (Tp) and $X^{21}$ is halogen, $C_1$-$C_3$-alkyl, or $C_1$-$C_3$-haloalkyl.

10. The compound according to claim 1, wherein T is (Tp) and $X^{24}$ is halogen, $C_1$-$C_3$-alkyl, or $C_1$-$C_3$-haloalkyl.

11. The compound according to claim 1, wherein $R^1$ is methyl, ethyl, propyl, or $C_1$-haloalkyl.

12. The compound according to claim 1, wherein $R^2$ is selected from the group consisting of hydrogen, $C_1$-$C_6$-alkyl, $C_1$-$C_6$-haloalkyl, $C_1$-$C_6$-alkoxy, $C_1$-$C_3$-alkoxy-$C_1$-$C_3$-alkyl, $C_3$-$C_6$-cycloalkyl, $C_2$-$C_6$-alkenyl, $C_2$-$C_6$-haloalkenyl, $C_2$-$C_6$-alkynyl and $C_2$-$C_6$-haloalkynyl.

13. A herbicidal composition comprising a herbicidal compound according to claim 1 and an agriculturally acceptable formulation adjuvant.

14. A herbicidal composition according to claim 13, further comprising at least one additional pesticide.

15. A method of controlling unwanted plant growth, comprising applying a compound of formula (I) as defined in claim 1, to the unwanted plants or to a locus thereof.

* * * * *